US009663795B2

(12) United States Patent
Meade et al.

(10) Patent No.: US 9,663,795 B2

(45) **Date of Patent: *May 30, 2017**

(54) USE OF CRY1AB IN COMBINATION WITH CRY1BE FOR MANAGEMENT OF RESISTANT INSECTS

(75) Inventors: Thomas Meade, Zionsville, IN (US); Kenneth Narva, Zionsville, IN (US); Nicholas P. Storer, Kensington, MD (US); Joel J. Sheets, Zionsville, IN (US); Aaron T. Woosley, Fishers, IN (US); Stephanie L. Burton, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 928 days.

This patent is subject to a terminal disclaimer.

(21) Appl. No.: 13/516,668

(22) PCT Filed: Dec. 16, 2010

(86) PCT No.: PCT/US2010/060830
§ 371 (c)(1),
(2), (4) Date: Aug. 30, 2012

(87) PCT Pub. No.: WO2011/084631
PCT Pub. Date: Jul. 14, 2011

(65) Prior Publication Data

US 2012/0324606 A1 Dec. 20, 2012

Related U.S. Application Data

(60) Provisional application No. 61/284,290, filed on Dec. 16, 2009.

(51) Int. Cl.

| | |
|---|---|
| *C12N 15/82* | (2006.01) |
| *A01H 5/00* | (2006.01) |
| *A01N 63/02* | (2006.01) |
| *A01N 65/00* | (2009.01) |

(52) U.S. Cl.
CPC ......... *C12N 15/8286* (2013.01); *A01N 63/02* (2013.01); *A01N 65/00* (2013.01)

(58) Field of Classification Search
None
See application file for complete search history.

(56) References Cited

U.S. PATENT DOCUMENTS

| | | | | |
|---|---|---|---|---|
| 5,723,758 A | | 3/1998 | Payne et al. | |
| 5,990,390 A | * | 11/1999 | Lundquist et al. | 800/302 |
| 6,218,188 B1 | * | 4/2001 | Cardineau et al. | 435/468 |
| 7,078,509 B2 | * | 7/2006 | Baum et al. | 536/23.1 |
| 2001/0026940 A1 | | 10/2001 | Cardineau et al. | |
| 2005/0155103 A1 | | 7/2005 | Baum et al. | |
| 2008/0311096 A1 | | 12/2008 | Lang et al. | |
| 2010/0269223 A1 | | 10/2010 | Lira et al. | |

FOREIGN PATENT DOCUMENTS

| | | | |
|---|---|---|---|
| WO | WO 00/26371 | * | 5/2000 |
| WO | WO 01/21821 | * | 3/2001 |
| WO | WO 2009/132850 | | 11/2009 |

OTHER PUBLICATIONS

Crickmore et al (2014 "Bacillus thuringiensis toxin nomenclature" http://www.btnomenclature.info/)).*
Hua et al (2001, Appl. Environ. Microbiol. 67:872-879).*
Denolf et al (1993, Appl. Environ. Microbiol. 59:1828-1837).*
Bates et al (2005, Nature Biotechnol. 23:57-62).*
Luo et al, 1999, Appl. Environ. Microbiol 65:457-464.*
Siqueira et al, 2004, J. Econ. Entomol. 97:1049-1057.*
Argolo-Filho et al, 2014, Insects 5:62-91.*

Bohorova et al., Novel synthetic Bacillus thuringiensis cry 1B gene and the cry1B-cry1Ab translational fusion confer resistance to southwestern corn borer, sugarcane borer and fall armyworm in transgenic tropical maize. Theor Appl Genet (2001), vol. 103, pp. 817-826. *especially abstract*.

UniProt Entry Q6PYW8. (online) 2007 [retrieved on Feb. 18, 2011] Retrieved from the internet <http://www.uniprot.org/uniprot/Q6PYW8>. See amino acid sequence and "DE Cry1B".

Schuphan et al., The European corn borer (*Ostrinia nubilalis*, Hbn.), its susceptibility to the Bt-toxin Cry1F, its pheromone races and its gene flow in Europe in view of an Insect Resistance Management. Darwin (online) Oct. 2009 [retrieved on Feb. 18, 2011]. Retrieved from the internet URL: <http://darwin.bth.rwth-aachen.de/opus3/volltexte/2010/3341/pdf/3341.pdf>. p. 10, para 2; p. 80, para 1 and 2.

Gutierrez et al., Physiologically based demographics of Bt cotton-pest interactions I. Pink bollworm resistance, refuge and risk. Eological Modelling, vol. 191 (2006), pp. 346-359. p. 353 Fig. 5.

Ahmad Awaar et al., Expression of synthetic cry1Ab and cry1Ac genes in Basmati rice (*Oryza sativa* L.) variety 370 via Agrobacterium-mediated transformation for the control of the European corn borer (*Ostrinia nubilalis*), In vitro cellular & Development Biology. Plant, Gaithersburg, MD, US, vol. 38, No. 2, Mar. 1, 2002 (Mar. 1, 2002), pp. 213-220, XP002711544. *the whole document*.

Bravo et al., How to cope with insect resistance to Bt toxins?, Trends in Biotechnology, Elsvier publications, Cambridge, GB, vol. 26, No. 10, Oct. 2, 2008, pp. 573-579, XP025406825. *the whole document*.

Sauka D.H., Benintende GB. Bacillus thuringiensis: generalidades. Un acercamlento a su empleo en el biocontrol de insectos lepidopteros que son plagas agricolas. Revista Argentina de Microbiologia. Apr.-Jun. 2008; 40(2): 124-40.

Rang, C. et al., Compeition of Bacillus thuringiensis Cry1 toxins for midgut binding sites: a basis for the development and management of transgenic tropical maize resistant to several stemborers, Curr. Microbiol., 2004, vol. 49, No. 1, pp. 22-27.

Gonzalez-Cabrera, J. et al., Toxicity and mode of action of Bacillus thuringiensis Cry proteins in the Mediterranean corn borer, *Sesamia nonagrioides* (Lefebvre)., Appl. Environ. Microbiol., 2006, vol. 72 No. 4, pp. 2594-2600.

Cui et al., "Insect-Resistance transgenic plant transformed with Bt Gene," *Journal of Agricultural Biotechnology*, 6(2):166-172 (Dec. 31, 1998) (English Abstract).

Pakula et al., "Genetic analysis of protein stability and function," *Annu. Rev. Genet.*, 23: 289-310 (1989).

Tabashnik et al., "Cross-Resistance of the Diamondback Moth Indicates Altered Interactions with Domain II of Bacillus thuringiensis Toxins," *Applied and Environmental Microbiology*, 62(8): 2839-2844 (1996).

Tabashnik et al., "One gene in diamondback moth confers resistance to four *Bacillus thuringiensis* toxins," *PNAS*, 94:1640-1644 (1997).

* cited by examiner

*Primary Examiner* — Anne Kubelik

(74) *Attorney, Agent, or Firm* — Ronald S. Maciak; Barnes & Thornburg LLP

(57) ABSTRACT

The subject invention includes methods and plants for controlling European corn borer and/or fall armyworm insects, said plants comprising a Cry1Ab insecticidal protein and a Cry1Be insecticidal protein, and various combinations of other proteins comprising this pair of proteins, to delay or prevent development of resistance by the insects.

19 Claims, 3 Drawing Sheets

Figure 2.

SEQUENCE LISTING

<160> NUMBER OF SEQ ID NOS: 2

<210> SEQ ID NO 1
<211> LENGTH: 641
<212> TYPE: PRT
<213> ORGANISM: Artificial Sequence
<220> FEATURE:
<223> OTHER INFORMATION: Cry1Be

<400> SEQUENCE: 1

```
Met Thr Ser Asn Arg Lys Asn Glu Asn Glu Ile Ile Asn Ala Leu Ser
1               5                   10                  15

Ile Pro Ala Val Ser Asn His Ser Ala Gln Met Asn Leu Ser Thr Asp
            20                  25                  30

Ala Arg Ile Glu Asp Ser Leu Cys Ile Ala Glu Gly Asn Asn Ile Asp
        35                  40                  45

Pro Phe Val Ser Ala Ser Thr Val Gln Thr Gly Ile Asn Ile Ala Gly
    50                  55                  60

Arg Ile Leu Gly Val Leu Gly Val Pro Phe Ala Gly Gln Ile Ala Ser
65                  70                  75                  80

Phe Tyr Ser Phe Leu Val Gly Glu Leu Trp Pro Arg Gly Arg Asp Pro
                85                  90                  95

Trp Glu Ile Phe Leu Glu His Val Glu Gln Leu Ile Arg Gln Gln Val
            100                 105                 110
```

```
Thr Glu Asn Thr Arg Asp Thr Ala Leu Ala Arg Leu Gln Gly Leu Gly
            115                 120                 125

Asn Ser Phe Arg Ala Tyr Gln Gln Ser Leu Glu Asp Trp Leu Glu Asn
        130                 135                 140

Arg Asp Asp Ala Arg Thr Arg Ser Val Leu Tyr Thr Gln Tyr Ile Ala
145                 150                 155                 160

Leu Glu Leu Asp Phe Leu Asn Ala Met Pro Leu Phe Ala Ile Arg Asn
                165                 170                 175

Gln Glu Val Pro Leu Leu Met Val Tyr Ala Gln Ala Ala Asn Leu His
                180                 185                 190

Leu Leu Leu Leu Arg Asp Ala Ser Leu Phe Gly Ser Glu Phe Gly Leu
            195                 200                 205

Thr Ser Gln Glu Ile Gln Arg Tyr Tyr Glu Arg Gln Val Glu Lys Thr
        210                 215                 220

Arg Glu Tyr Ser Asp Tyr Cys Ala Arg Trp Tyr Asn Thr Gly Leu Asn
225                 230                 235                 240

Asn Leu Arg Gly Thr Asn Ala Glu Ser Trp Leu Arg Tyr Asn Gln Phe
                245                 250                 255

Arg Arg Asp Leu Thr Leu Gly Val Leu Asp Leu Val Ala Leu Phe Pro
                260                 265                 270

Ser Tyr Asp Thr Arg Val Tyr Pro Met Asn Thr Ser Ala Gln Leu Thr
            275                 280                 285

Arg Glu Ile Tyr Thr Asp Pro Ile Gly Arg Thr Asn Ala Pro Ser Gly
        290                 295                 300

Phe Ala Ser Thr Asn Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Phe Ser Val Leu Ser Arg Trp Ser Asn Thr Gln Tyr
            340                 345                 350

Met Asn Tyr Trp Val Gly His Arg Leu Glu Ser Arg Thr Ile Arg Gly
        355                 360                 365

Ser Leu Ser Thr Ser Thr His Gly Asn Thr Asn Thr Ser Ile Asn Pro
370                 375                 380

Val Thr Leu Gln Phe Thr Ser Arg Asp Val Tyr Arg Thr Glu Ser Phe
385                 390                 395                 400

Ala Gly Ile Asn Ile Leu Leu Thr Thr Pro Val Asn Gly Val Pro Trp
                405                 410                 415

Ala Arg Phe Asn Trp Arg Asn Pro Leu Asn Ser Leu Arg Gly Ser Leu
                420                 425                 430

Leu Tyr Thr Ile Gly Tyr Thr Gly Val Gly Thr Gln Leu Phe Asp Ser
            435                 440                 445

Glu Thr Glu Leu Pro Pro Glu Thr Thr Glu Arg Pro Asn Tyr Glu Ser
        450                 455                 460

Tyr Ser His Arg Leu Ser Asn Ile Arg Leu Ile Ser Gly Asn Thr Leu
465                 470                 475                 480

Arg Ala Pro Val Tyr Ser Trp Thr His Arg Ser Ala Asp Arg Thr Asn
                485                 490                 495

Thr Ile Ser Ser Asp Ser Ile Thr Gln Ile Pro Leu Val Lys Ser Phe
            500                 505                 510

Asn Leu Asn Ser Gly Thr Ser Val Val Ser Gly Pro Gly Phe Thr Gly
            515                 520                 525
```

```
Gly Asp Ile Ile Arg Thr Asn Val Asn Gly Ser Val Leu Ser Met Gly
        530                 535                 540
Leu Asn Phe Asn Asn Thr Ser Leu Gln Arg Tyr Arg Val Arg Val Arg
545                 550                 555                 560
Tyr Ala Ala Ser Gln Thr Met Val Leu Arg Val Thr Val Gly Gly Ser
                565                 570                 575
Thr Thr Phe Asp Gln Gly Phe Pro Ser Thr Met Ser Ala Asn Glu Ser
            580                 585                 590
Leu Thr Ser Gln Ser Phe Arg Phe Ala Glu Phe Pro Val Gly Ile Ser
                595                 600                 605
Ala Ser Gly Ser Gln Thr Ala Gly Ile Ser Ile Ser Asn Asn Ala Gly
            610                 615                 620
Arg Gln Thr Phe His Phe Asp Lys Ile Glu Phe Ile Pro Ile Thr Ala
625                 630                 635                 640
Thr
```

<210> SEQ ID NO 2
<211> LENGTH: 612
<212> TYPE: PRT
<213> ORGANISM: Artificial Sequence
<220> FEATURE:
<223> OTHER INFORMATION: Cry1Ab

<400> SEQUENCE: 2

```
Met Asp Asn Asn Pro Asn Ile Asn Glu Cys Ile Pro Tyr Asn Cys Leu
1                   5                   10                  15
Ser Asn Pro Glu Val Glu Val Leu Gly Gly Glu Arg Ile Glu Thr Gly
                20                  25                  30
Tyr Thr Pro Ile Asp Ile Ser Leu Ser Leu Thr Gln Phe Leu Leu Ser
            35                  40                  45
Glu Phe Val Pro Gly Ala Gly Phe Val Leu Gly Leu Val Asp Ile Ile
        50                  55                  60
Trp Gly Ile Phe Gly Pro Ser Gln Trp Asp Ala Phe Leu Val Gln Ile
65                  70                  75                  80
Glu Gln Leu Ile Asn Gln Arg Ile Glu Glu Phe Ala Arg Asn Gln Ala
                85                  90                  95
Ile Ser Arg Leu Glu Gly Leu Ser Asn Leu Tyr Gln Ile Tyr Ala Glu
            100                 105                 110
Ser Phe Arg Glu Trp Glu Ala Asp Pro Thr Asn Pro Ala Leu Arg Glu
        115                 120                 125
Glu Met Arg Ile Gln Phe Asn Asp Met Asn Ser Ala Leu Thr Thr Ala
    130                 135                 140
Ile Pro Leu Phe Ala Val Gln Asn Tyr Gln Val Pro Leu Leu Ser Val
145                 150                 155                 160
Tyr Val Gln Ala Ala Asn Leu His Leu Ser Val Leu Arg Asp Val Ser
                165                 170                 175
Val Phe Gly Gln Arg Trp Gly Phe Asp Ala Ala Thr Ile Asn Ser Arg
            180                 185                 190
Tyr Asn Asp Leu Thr Arg Leu Ile Gly Asn Tyr Thr Asp Tyr Ala Val
        195                 200                 205
Arg Trp Tyr Asn Thr Gly Leu Glu Arg Val Trp Gly Pro Asp Ser Arg
    210                 215                 220
Asp Trp Val Arg Tyr Asn Gln Phe Arg Arg Glu Leu Thr Leu Thr Val
225                 230                 235                 240
Leu Asp Ile Val Ala Leu Phe Pro Asn Tyr Asp Ser Arg Arg Tyr Pro
```

-continued

```
                245                 250                 255
Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
                275                 280                 285

Arg Ser Ile Arg Ser Pro His Leu Met Asp Ile Leu Asn Ser Ile Thr
                290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
                340                 345                 350

Gln Leu Gly Gln Gly Val Tyr Arg Thr Leu Ser Ser Thr Leu Tyr Arg
                355                 360                 365

Arg Pro Phe Asn Ile Gly Ile Asn Asn Gln Gln Leu Ser Val Leu Asp
                370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
                420                 425                 430

Val Ser Met Phe Arg Ser Gly Phe Ser Asn Ser Ser Val Ser Ile Ile
                435                 440                 445

Arg Ala Pro Met Phe Ser Trp Ile His Arg Ser Ala Glu Phe Asn Asn
                450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
                515                 520                 525

Tyr Ala Ser Thr Thr Asn Leu Gln Phe His Thr Ser Ile Asp Gly Arg
                530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
                595                 600                 605

Val Thr Phe Glu
                610
```

USE OF CRY1AB IN COMBINATION WITH CRY1BE FOR MANAGEMENT OF RESISTANT INSECTS

CROSS-REFERENCE TO RELATED APPLICATIONS

This is a national phase application, filed pursuant to 35 U.S.C. §371, of PCT application No. PCT/US2010/060830, filed on Dec. 16, 2010, which claims the benefit of U.S. provisional application No. 61/284,290, filed on Dec. 16, 2009. The prior applications are incorporated herein by reference in their entirety.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1F and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm). See also U.S. Patent Application Publication No. 2009/0313717, which relates to a Cry2 protein plus a Vip3Aa, Cry1F, or Cry1A for control of *Helicoverpa zea* or *armigerain*. WO 2009/132850 relates to Cry1F or Cry1A and Vip3Aa for controlling *Spodoptera frugiperda*. U.S. Patent Application Publication No. 2008/0311096 relates in part to Cry1Ab for controlling Cry1F-resistant European corn borer (ECB; *Ostrinia nubilalis* (Hübner)).

That is, some of the qualities of insect-resistant transgenic plants that have led to rapid and widespread adoption of this technology also give rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an insect resistant management (IRM) stack need to exert their insecticidal effect independently so that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor in an insect, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is cross-resistant to both Bt toxins. However, if two toxins bind to two different receptors, this could be an indication that the insect would not be simultaneously resistant to those two toxins.

For example, Cry1Fa protein is useful in controlling many lepidopteran pests species including ECB and the fall armyworm (FAW; *Spodoptera frugiperda*), and is active against the sugarcane borer (SCB; *Diatraea saccharalis*). The Cry1Fa protein, as produced in transgenic corn plants containing event TC1507, is responsible for an industry-leading insect resistance trait for FAW control. Cry1Fa is further deployed in the Herculex®, SmartStax™, and WideStrike™ products.

The ability to conduct (competitive or homologous) receptor binding studies using Cry1Fa protein has been limited because a common technique available for labeling proteins for detection in receptor binding assays tends to inactivate the insecticidal activity of the Cry1Fa protein.

Additional Cry toxins are listed at the website of the official B.t. nomenclature committee (Crickmore et al.; lifesci.sussex.ac.uldhome/Neil_Crickmore/Bt/). There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the surprising discovery that Cry1Ab and Cry1Be do not compete for binding to sites in European corn borer (ECB; *Ostrinia nubilalis* (Hübner)) or fall armyworm (FAW; *Spodoptera frugiperda*) gut cell membrane preparations. As one skilled in the art will recognize with the benefit of this disclosure, plants that produce both of these proteins (including insecticidal portions of the full-length proteins) can delay or prevent the development of resistance to any of these insecticidal proteins alone. Corn and soybean are some preferred plants. ECB is the preferred target insect for the subject pair of toxins.

Thus, the subject invention relates in part to the use of a Cry1Ab protein in combination with a Cry1Be protein. Plants (and acreage planted with such plants) that produce both of these proteins are included within the scope of the subject invention.

The subject invention also relates in part to triple stacks or "pyramids" of three (or more) toxins, with Cry1Ab and Cry1Be being the base pair. In some preferred pyramid embodiments, the combination of the selected toxins provides three sites of action against ECB. Some preferred "three sites of action" pyramid combinations include the subject base pair of proteins plus Cry2A, Cry1I, and DIG-3 as the third protein for targeting ECB. These particular triple stacks would, according to the subject invention, advantageously and surprisingly provide three sites of action against ECB. This can help to reduce or eliminate the requirement for refuge acreage.

Although the subject invention is disclosed herein as a base pair of toxins, Cry1Ab and Cry1Be, which, either alone or in a "pyramid" of three or more toxins, provides for insect-resistance against ECB in corn, it should be understood that the combinations of Cry1Ab and Cry1Be, described herein, can be also used with additional proteins for targeting FAW in both soybean or corn.

Additional toxins/genes can also be added according to the subject invention. For example, if Cry1Fa is stacked with the subject pair of proteins (Cry1Fa and Cry1Be are both active against both FAW and ECB), adding one additional protein to this triple stack wherein the fourth added protein targets ECB, would provide three sites of action against FAW, and three sites of action against ECB. This added protein (the fourth protein for targeting FAW) could be selected from the group consisting of Cry1Fa, Vip3Ab, or Cry1E. This would result in a four-protein stack having three sites of action against two insects (ECB and FAW).

BRIEF DESCRIPTION OF THE TABLES

Table 1: provides examples of Amino Acids within the Four Classes of Amino Acids.

BRIEF DESCRIPTION OF THE FIGURES

FIG. 2: is a graph illustrating the percent binding of labeled Cry1Ab versus Cry1Be with FAW BBMVs.

DETAILED DESCRIPTION OF THE INVENTION

Figure 1:
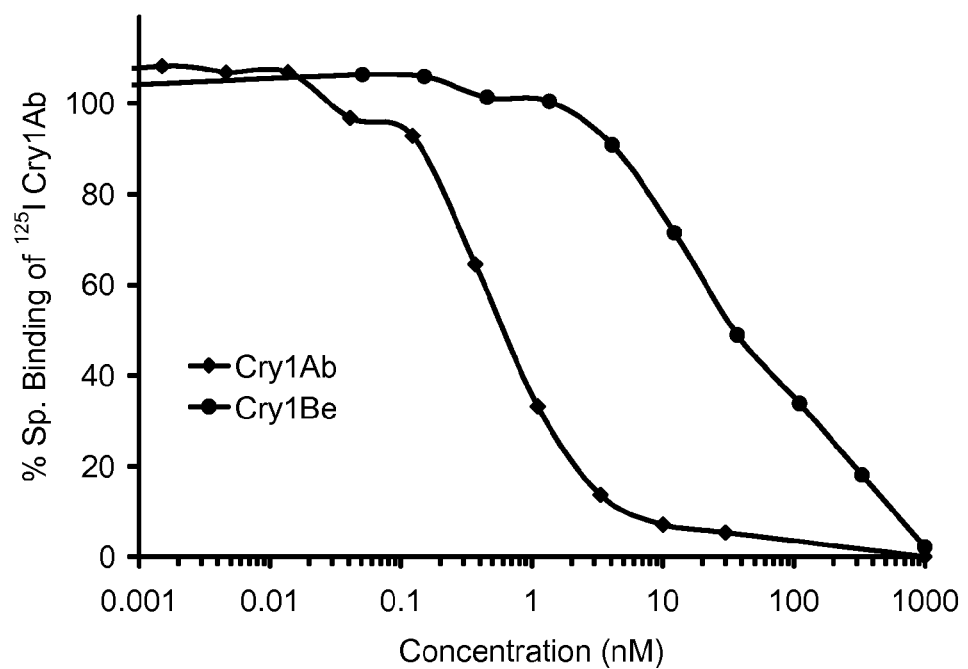
FIG. 1: is a graph illustrating the percent binding of labeled Cry1Ab versus Cry1Be for ECB BBMVs.

The subject invention relates in part to the surprising discovery that Cry1Ab and Cry1Be do not compete with each other for binding sites in the gut of the European corn borer (ECB; *Ostrinia nubilalis* (Hübner)) or the fall armyworms (FAW; *Spodoptera frugiperda*). Thus, a Cry1Ab protein can be used in combination with a Cry1Be protein in transgenic corn (and other plants; e.g., cotton and soybeans, for example) to delay or prevent ECB from developing resistance to either of these proteins alone. The subject pair of proteins can be effective at protecting plants (such as maize plants) from damage by Cry-resistant ECB. That is, one use of the subject invention is to protect corn and other economically important plant species from damage and yield loss caused by ECB populations that could develop resistance to Cry1Ab or Cry1Be.

The subject invention thus teaches an insect resistant management (IRM) stack comprising Cry1Ab and Cry1Be to prevent or mitigate the development of resistance by ECB to either or both of these proteins.

Further, although the subject invention, disclosed herein, teaches an IRM stack comprising Cry1Ab and Cry1Be for preventing resistance by ECB to either or both of these proteins, it is within the scope of the invention disclosed herein that one or both of Cry1Ab and Cry1Be may be adapted, either alone or in combination, to prevent resistance by FAW to either or both of these proteins.

The present invention provides compositions for controlling lepidopteran pests comprising cells that produce a Cry1Ab core toxin-containing protein and a Cry1Be core toxin-containing protein.

The invention further comprises a host transformed to produce both a Cry1Ab insecticidal protein and a Cry1Be insecticidal protein, wherein said host is a microorganism or a plant cell. The subject polynucleotide(s) are preferably in a genetic construct under control of a non-*Bacillus-thuringiensis* promoter(s). The subject polynucleotides can comprise codon usage for enhanced expression in a plant.

It is additionally intended that the invention provides a method of controlling lepidopteran pests comprising contacting said pests or the environment of said pests with an effective amount of a composition that contains a Cry1Ab insecticidal protein and further contains a Cry1Be insecticidal protein.

An embodiment of the invention comprises a maize plant comprising a plant-expressible gene encoding a Cry1Be core toxin-containing protein and a plant-expressible gene encoding a Cry1Ab core toxin-containing protein, and seed of such a plant.

A further embodiment of the invention comprises a maize plant wherein a plant-expressible gene encoding a Cry1Be insecticidal protein and a plant-expressible gene encoding a Cry1Ab insecticidal protein have been introgressed into said maize plant, and seed of such a plant.

As described in the Examples, competitive receptor binding studies using radiolabeled Cry1Ab and Cry1Be proteins show that the Cry1Be protein does not compete for binding in ECB or FAW tissues to which Cry1Ab binds. These results also indicate that the combination of Cry1Ab and Cry1Be proteins can be an effective means to mitigate the development of resistance in ECB and FAW populations to either of these proteins. Thus, based in part on the data described herein, it is thought that co-production (stacking) of the Cry1Be and Cry1Ab proteins can be used to produce a high dose IRM stack for ECB.

Other proteins can be added to this pair. For example, the subject invention also relates in part to triple stacks or "pyramids" of three (or more) toxins, with Cry1Ab and Cry1Be being the base pair. In some preferred pyramid embodiments, the selected toxins have three separate sites of action against FAW. Some preferred "three sites of action" pyramid combinations include the subject base pair of proteins plus Cry1Fa, Vip3Ab, Cry1C, Cry1 D, or Cry1E as the third protein for targeting FAW. These particular triple stacks would, according to the subject invention, advantageously and surprisingly provide three sites of action against FAW. This can help to reduce or eliminate the requirement for refuge acreage. By "separate sites of action," it is meant any of the given proteins do not cause cross-resistance with each other.

Additional toxins/genes can also be added according to the subject invention. For example, if Cry1Fa is stacked with the subject pair of proteins (both Cry1Fa and Cry1Be are both active against both FAW and European cornborer (ECB)), adding one additional protein to this triple stack wherein the fourth added protein targets ECB, would provide three sites of action against FAW, and three sites of action against ECB. This added protein (the fourth protein) could be selected from the group consisting of Cry2A, Cry1 I, and DIG-3 (see U.S. Patent Application Ser. No. 61/284,278 (filed Dec. 16, 2009) and US 2010 00269223). This would result in a four-protein stack having three sites of action against two insects (ECB and FAW).

Thus, one deployment option is to use the subject pair of proteins in combination with a third toxin/gene, and to use this triple stack to mitigate the development of resistance in ECB and/or FAW to any of these toxins. Accordingly, the subject invention also relates in part to triple stacks or "pyramids" of three (or more) toxins. In some preferred pyramid embodiments, the selected toxins have three separate sites of action against ECB and/or FAW.

Included among deployment options of the subject invention would be to use two, three, or more proteins of the subject proteins in crop-growing regions where ECB and/or FAW can develop resistant populations.

For guidance regarding the use of Cry1Fa and Cry1Be (for controlling ECB and/or FAW), see U.S. Patent Application Ser. No. 61/284,290 (filed Dec. 16, 2009). With Cry1Fa being active against ECB (and FAW), Cry1Ab plus Cry1Be plus Cry1 Fa would, according to the subject invention, advantageously and surprisingly provide three sites of action against ECB. This can help to reduce or eliminate the requirement for refuge acreage.

Cry1 Fa is deployed in the Herculex®, SmartStax™, and WidesStrike™ products. The subject pair of genes (Cry1Ab and Cry1Be) could be combined into, for example, a Cry1Fa product such as Herculex®, SmartStax™, and WideStrike™. Accordingly, the subject pair of proteins could be significant in reducing the selection pressure on these and other proteins. The subject pair of proteins could thus be used as in the three gene combinations for corn and other plants (cotton and soybeans, for example).

As discussed above, additional toxins/genes can also be added according to the subject invention. For targeting ECB, Cry2A, Cry1I, and/or DIG-3 can be used. See U.S. Patent Application Ser. No. 61/284,278 (filed Dec. 16, 2009) and US 2010 00269223. For the combination of Cry1F and Cry1Ab (for controlling ECB), see U.S. Patent Application Publication No. 2008/0311096.

Plants (and acreage planted with such plants) that produce any of the subject combinations of proteins are included within the scope of the subject invention. Additional toxins/genes can also be added, but the particular stacks discussed above advantageously and surprisingly provide multiple sites of action against ECB and/or FAW. This can help to reduce or eliminate the requirement for refuge acreage. A field thus planted of over ten acres is thus included within the subject invention.

GENBANK can also be used to obtain the sequences for any of the genes and proteins discussed herein. See Appendix A, below. Patents can also be used. For example, U.S. Pat. No. 5,188,960 and U.S. Pat. No. 5,827,514 describe Cry1Fa core toxin containing proteins suitable for use in carrying out the present invention. U.S. Pat. No. 6,218,188 describes plant-optimized DNA sequences encoding Cry1Fa core toxin-containing proteins that are suitable for use in the present invention.

Combinations of proteins described herein can be used to control lepidopteran pests. Adult lepidopterans, for example, butterflies and moths, primarily feed on flower nectar and are a significant effector of pollination. Nearly all lepidopteran larvae, i.e., caterpillars, feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value. As used herein, reference to lepidopteran pests refers to various life stages of the pest, including larval stages.

Some chimeric toxins of the subject invention comprise a full N-terminal core toxin portion of a Bt toxin and, at some point past the end of the core toxin portion, the protein has a transition to a heterologous protoxin sequence. The N-terminal, insecticidally active, toxin portion of a Bt toxin is referred to as the "core" toxin. The transition from the core toxin segment to the heterologous protoxin segment can occur at approximately the toxin/protoxin junction or, in the alternative, a portion of the native protoxin (extending past the core toxin portion) can be retained, with the transition to the heterologous protoxin portion occurring downstream.

As an example, one chimeric toxin of the subject invention, is a full core toxin portion of Cry1Ab (approximately amino acids 1 to 601) and/or a heterologous protoxin (approximately amino acids 602 to the C-terminus). In one preferred embodiment, the portion of a chimeric toxin comprising the protoxin is derived from a Cry1Ab protein toxin. In a preferred embodiment, the portion of a chimeric toxin comprising the protoxin is derived from a Cry1Ab protein toxin.

A person skilled in this art will appreciate that Bt toxins, even within a certain class such as Cry1Be, will vary to some extent in length and the precise location of the transition from core toxin portion to protoxin portion. Typically, the Cry1Be toxins are about 1150 to about 1200 amino acids in length. The transition from core toxin portion to protoxin portion will typically occur at between about 50% to about 60% of the full length toxin. The chimeric toxin of the subject invention will include the full expanse of this N-terminal core toxin portion. Thus, the chimeric toxin will comprise at least about 50% of the full length of the Cry1Be protein. This will typically be at least about 590 amino acids. With regard to the protoxin portion, the full expanse of the Cry1 Ab protoxin portion extends from the end of the core toxin portion to the C-terminus of the molecule.

Genes and Toxins.

The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Ab's and Cry1Be's), 78% (Cry1A's and Cry1B's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only.

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino, acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant Toxins.

Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Below is a listing of examples of amino acids belonging to each class.

TABLE 1

Examples of Amino Acids within the Four Classes of Amino Acids

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant Hosts.

The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the Bt toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces,*

*Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods is available for introducing a Bt gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of Cells.

*Bacillus thuringiensis* or recombinant cells expressing the Bt toxins can be treated to prolong the toxin activity and stabilize the cell. The pesticide microcapsule that is formed comprises the Bt toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the Bt toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will cross-link proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the Bt gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of Cells.

The cellular host containing the Bt insecticidal gene or genes may be grown in any convenient nutrient medium, where the DNA construct provides a selective advantage, providing for a selective medium so that substantially all or all of the cells retain the Bt gene. These cells may then be harvested in accordance with conventional ways. Alternatively, the cells can be treated prior to harvesting.

The Bt cells producing the toxins of the invention can be cultured using standard art media and fermentation techniques. Upon completion of the fermentation cycle the bacteria can be harvested by first separating the Bt spores and crystals from the fermentation broth by means well known in the art. The recovered Bt spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations.

Formulated bait granules containing an attractant and spores, crystals, and toxins of the Bt isolates, or recombinant microbes comprising the genes obtainable from the Bt isolates disclosed herein, can be applied to the soil. Formulated product can also be applied as a seed-coating or root treatment or total plant treatment at later stages of the crop cycle. Plant and soil treatments of Bt cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant Transformation.

A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13 mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If *Agrobacteria* are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in *Agrobacteria*. The intermediate vector can be transferred into *Agrobacterium tumefaciens* by means of a helper plasmid (conjugation). Binary vectors can replicate themselves both in *E. coli* and in *Agrobacteria*. They comprise a selection marker gene and a linker or polylinker which are framed by the Right and Left T-DNA border regions. They can be transformed directly into *Agrobacteria* (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. No. 6,218,188 and U.S. Pat. No. 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Ab protein, and further comprising a second plant expressible gene encoding a Cry1Be protein.

Transfer (or introgression) of the Cry1Ab- and Cry1Be-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1A- and Cry1Be-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies.

Roush et al., for example, outlines two-toxin strategies, also called "pyramiding" or "stacking," for management of insecticidal transgenic crops. (The Royal Society. *Phil. Trans. R. Soc. Lond. B.* (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a section of non-Bt crops/corn) for use with transgenic crops producing a single Bt protein active against target pests.

"The specific structured requirements for corn borer-protected Bt (Cry1Ab or Cry1F) corn products are as follows:
Structured refuges: 20% non-Lepidopteran Bt corn refuge in Corn Belt;
50% non-Lepidopteran Bt refuge in Cotton Belt
Blocks
  internal (i.e., within the Bt field)
  External (i.e., separate fields within V2 mile (¼ mile if possible) of the
  Bt field to maximize random mating)
In-Field Strips
  Strips must be at least 4 rows wide (preferably 6 rows) to reduce the effects of larval movement"

In addition, the National Corn Growers Association, on their website:
(ncga.com/insect-resistance-management-fact-sheet-bt-corn)
It also provides similar guidance regarding the refuge requirements. For example:
"Requirements of the Corn Borer IRM:
  Plant at least 20% of your corn acres to refuge hybrids
  In cotton producing regions, refuge must be 50%
  Must be planted within ½ mile of the refuge hybrids
  Refuge can be planted as strips within the Bt field; the refuge strips must be at least 4 rows wide
  Refuge may be treated with conventional pesticides only if economic thresholds are reached for target insect
  Bt-based sprayable insecticides cannot be used on the refuge corn
  Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three sites of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLES

Example 1

$^{125}$I Labeling of Cry Proteins

Iodination of Cry Toxins.

Purified truncated Cry toxins were was iodinated using Iodo-Beads or Iodo-gen (Pierce). Briefly, two Iodo-Beads were washed twice with 500 µl of phosphate buffered saline, PBS (20 mM sodium phosphate, 0.15 M NaCl, pH 7.5), and placed into a 1.5 ml centrifuge tube behind lead shielding. To this was added 100 µl of PBS. In a hood and through the use of proper radioactive handling techniques, 0.5 mCi Na$^{125}$I (17.4 Ci/mg, Lot 0114, Amersham) was added to the PBS solution with the Iodo-Bead. The components were allowed to react for 5 minutes at room temperature, then 2-25 µg of highly pure truncated Cry protein was added to the solution and allowed to react for an additional 3-5 minutes. The reaction was terminated by removing the solution from the iodo-beads and applying it to a 0.5 ml desalting Zeba spin column (InVitrogen) equilibrated in PBS. The iodo-bead was washed twice with 10 µl of PBS each and the wash solution also applied to the desalting column. The radioactive solution was eluted through the desalting column by centrifugation at 1,000×g for 2 min. In the case of Cry1Da, the Iodo-gen method was used to conduct the radiolabeling procedure. Using this procedure, the cry toxin in 100 mM phosphate buffer (pH 8) was first cleaned of lipopolysaccharides (LPS) by passing it through a small 0.5 ml polymyxin column multiple times. To the iodo-gen tube (Pierce Chem. Co.) was added 20 µg of the LPS-free Cry1Da toxin, then 0.5 mCi of Na$^{125}$I. The reaction mixture was shaken for 15 min at 25° C. The solution was removed from the tube, and 50 µl of 0.2M non-radiolabeled NaI added to quench the reaction. The protein was dialyzed vs PBS with 3 changes of buffer to remove any unbound $^{125}$I.

Radio-purity of the iodinated Cry proteins was determined by SDS-PAGE, phosphorimaging and gamma counting. Briefly, 2 µl of the radioactive protein was separated by SDS-PAGE. After separation, the gels were dried using a BioRad gel drying apparatus following the manufacturer's instructions. The dried gels were imaged by wrapping them in Mylar film (12 µm thick), and exposing them under a Molecular Dynamics storage phosphor screen (35 cm×43 cm), for 1 hour. The plates were developed using a Molecular Dynamics Storm 820 phosphorimager and the imaged analyzed using ImageQuant™ software. The radioactive band along with areas immediately above and below the band were cut from the gel using a razor blade and counted in a gamma counter. Radioactivity was only detected in the Cry protein band and in areas below the band. No radioactivity was detected above the band, indicating that all radioactive contaminants consisted of smaller protein components than the truncated Cry protein. These components most probably represent degradation products.

Example 2

BBMV Preparation Protocol

Preparation and Fractionation of Solubilized BBMV's.

Last instar *Spodoptera frugiperda, Ostrinia nubilalis*, or *Heleothis zea* larvae were fasted overnight and then dissected in the morning after chilling on ice for 15 minutes. The midgut tissue was removed from the body cavity, leaving behind the hindgut attached to the integument. The midgut was placed in 9× volume of ice cold homogenization buffer (300 mM mannitol, 5 mM EGTA, 17 mM tris. base, pH 7.5), supplemented with Protease Inhibitor Cocktail[1] (Sigma P-2714) diluted as recommended by the supplier. The tissue was homogenized with 15 strokes of a glass tissue homogenizer. BBMV's were prepared by the $MgCl_2$ precipitation method of Wolfersberger (1993). Briefly, an equal volume of a 24 mM $MgCl_2$ solution in 300 mM mannitol was mixed with the midgut homogenate, stirred for 5 minutes and allowed to stand on ice for 15 min. The solution was centrifuged at 2,500×g for 15 min at 4° C. The supernatant was saved and the pellet suspended into the original volume of 0.5-× diluted homogenization buffer and centrifuged again. The two supernatants were combined, centrifuged at 27,000×g for 30 min at 4° C. to form the BBMV fraction. The pellet was suspended into 10 ml homogienization buffer and supplemented to protease inhibitiors and centrifuged again at 27,000×g of r30 min at 4° C. to wash the BBMV's. The resulting pellet was suspended into BBMV Storage Buffer (10 mM HEPES, 130 mM KCl, 10% glycerol, pH 7.4) to a concentration of about 3 mg/ml protein. Protein concentration was determined by using the Bradford method (1976) with bovine serum albumin (BSA) as the standard. Alkaline phosphatase determination was made prior to freezing the samples using the Sigma assay following manufacturer's instructions. The specific activity of this marker enzyme in the BBMV fraction typically increased 7-fold compared to that found in the midgut homogenate fraction. The BBMV's were aliquoted into 250 µl samples, flash frozen in liquid $N_2$ and stored at −80° C.

Final concentration of cocktail components (in µM) are AEBSF (500), EDTA (250 mM), Bestatin (32), E-64 (0.35). Leupeptin (0.25), and Aprotinin (0.075).

Example 3

Method to Measure Binding of $^{125}I$ Cry Proteins to BBMV Proteins

Binding of $^{125}I$ Cry Proteins to BBMV's.

To determine the optimal amount of BBMV protein to use in the binding assays, a saturation curve was generated. $^{125}I$ radiolabeled Cry protein (0.5 nM) was incubated for 1 hr. at 28° C. with various amounts of BBMV protein, ranging from 0-500 µg/ml in binding buffer (8 mM $NaHPO_4$, 2 mM $KH_2PO_4$, 150 mM NaCl, 0.1% bovine serum albumin, pH 7.4). Total volume was 0.5 ml. Bound $^{125}I$ Cry protein was separated from unbound by sampling 150 µl of the reaction mixture in triplicate from a 1.5 ml centrifuge tube into a 500 µl centrifuge tube and centrifuging the samples at 14,000×g for 6 minutes at room temperature. The supernatant was gently removed, and the pellet gently washed three times with ice cold binding buffer. The bottom of the centrifuge containing the pellet was cut out and placed into a 13×75-mm glass culture tube. The samples were counted for 5 minutes each in the gamma counter. The counts contained in the sample were subtracted from background counts (reaction with out any protein) and was plotted versus BBMV protein concentration. The optimal amount of protein to use was determined to be 0.15 mg/ml of BBMV protein.

To determine the binding kinetics, a saturation curve was generated. Briefly, BBMV's (150 µg/ml) were incubated for 1 hr. at 28° C. with increasing concentrations of $^{125}I$ Cry toxin, ranging from 0.01 to 10 nM. Total binding was determined by sampling 150 µl of each concentration in triplicate, centrifugation of the sample and counting as described above. Non-specific binding was determined in the same manner, with the addition of 1,000 nM of the homologous trypsinized non-radioactive Cry toxin added to the reaction mixture to saturate all non-specific receptor binding sites. Specific binding was calculated as the difference between total binding and non-specific binding.

Homologous and heterologous competition binding assays were conducted using 150 µg/ml BBMV protein and 0.5 nM of the $^{125}I$ radiolabeled Cry protein. The concentration of the competitive non-radiolabeled Cry toxin added to the reaction mixture ranged from 0.045 to 1,000 nM and were added at the same time as the radioactive ligand, to assure true binding competition. Incubations were carried out for 1 hr. at 28° C. and the amount of $^{125}I$ Cry protein bound to its receptor toxin measured as described above with non-specific binding subtracted. One hundred percent total binding was determined in the absence of any competitor ligand. Results were plotted on a semi-logarithmic plot as percent total specific binding versus concentration of competitive ligand added.

Example 4

Summary of Results

FIG. 1 shows percent specific binding of $^{125}I$ Cry1Ab (0.5 nM) in BBMV's from ECB versus competition by unlabeled homologous Cry1Ab (♦) and heterologous Cry1Be (●). The displacement curve for homologous competition by Cry1Ab results in a sigmoidal shaped curve showing 50% displacement of the radioligand at about 0.5 nM of Cry1Ab. Cry1Be also displaces $^{125}I$ Cry1Be from its binding site but requires approximately 40 nM concentration (80-fold higher than required by Cry1Ab), to displace 50% of the $^{125}I$ Cry1Ab from its binding site.

Figure 2:
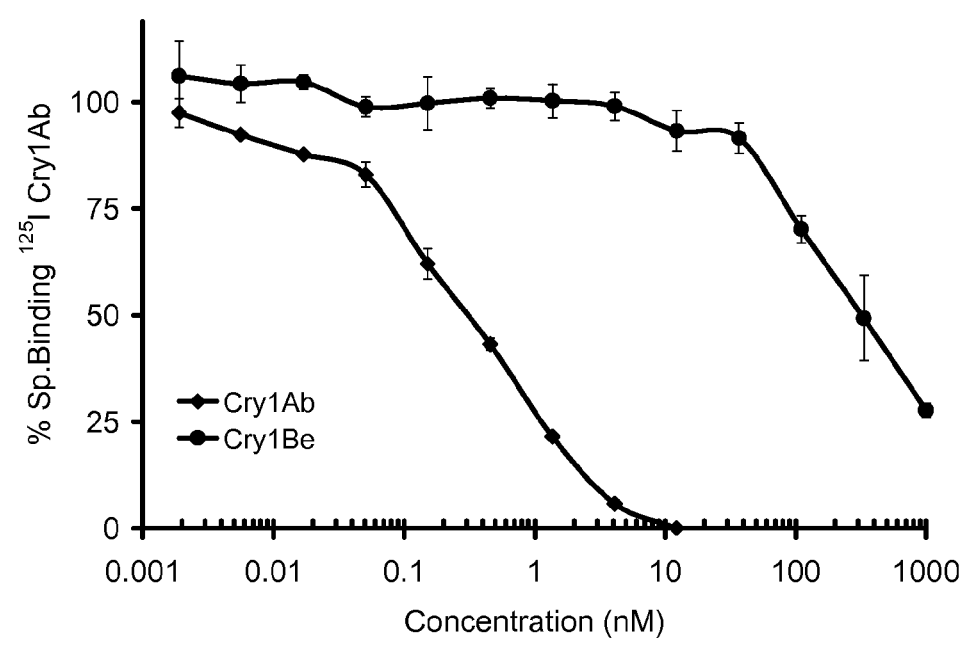

FIG. 2 shows percent specific binding of $^{125}I$ Cry1Ab (0.5 nM) in BBMV's from FAW versus competition by unlabeled homologous Cry1Ab (♦) and heterologous Cry1Be (●). The displacement curve for homologous competition by Cry1Ab results in a sigmoidal shaped curve showing 50% displacement of the radioligand at about 0.3 nM of Cry1Ab. Cry1Be displaces $^{125}I$ Cry1Ab by 50% at a concentration of approximately 300 nM, or about 1,000-fold greater than required by Cry1Ab. Error bars represent the range of values obtained from duplicate determinations.

Figure 3:
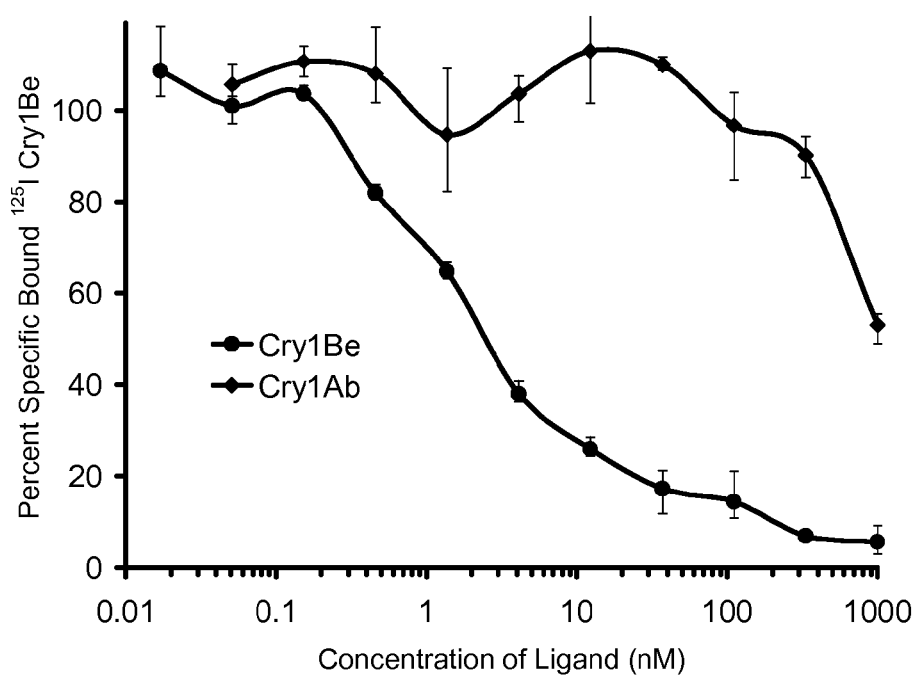
FIG. 3: is a graph illustrating the percent binding of labeled Cry1Be versus Cry1Ab with FAW BBMVs.

FIG. 3 shows percent specific binding of $^{125}I$ Cry1Be (0.5 nM) in BBMV's from FAW versus competition by unlabeled homologous Cry1Be (♦) and heterologous Cry1Ab (●). The displacement curve for homologous competition by Cry1Be results in a sigmoidal shaped curve showing 50% displacement of the radioligand at about 2 nM of Cry1Be. Cry1Ab at a concentration of 1,000 nM (2,000-fold greater than $^{125}I$ Cry1Be being displaced) results approximately 50% displacement. There is an approximate 500-fold lower affinity of Cry1Ab to compete for the binding of Cry1Be. Error bars represent the range of values obtained from triplicate determinations.

REFERENCE LIST

Heckel, D. G., Gahan, L. J., Baxter, S. W., Zhao, J. Z., Shelton, A. M., Gould, F., and Tabashnik, B. E. (2007). The diversity of Bt resistance genes in species of Lepidoptera. J Invertebr Pathol 95, 192-197.

Luo, K., Banks, D., and Adang, M. J. (1999). Toxicity, binding, and permeability analyses of four *bacillus thuringiensis* cry1 delta-endotoxins using brush border membrane vesicles of *spodoptera exigua* and *spodoptera frugiperda*. Appl. Environ. Microbiol. 65, 457-464.

Palmer, M., Buchkremer, M, Valeva, A, and Bhakdi, S. Cysteine-specific radioiodination of proteins with fluorescein maleimide. Analytical Biochemistry 253, 175-179. 1997. Ref Type: Journal (Full)

Sambrook, J. and Russell, D. W. (2001). Molecular Cloning: A Laboratory Manual. Cold Spring Harbor Laboratory).

Schlenz, M. L., Babcock, J. M., and Storer, N. P. Response of Cry1F-resistant and Susceptible European Corn Borer and Fall Armyworm Colonies to Cry1A. 105 and Cry12Ab2. DAI 0830, 2008. Indianapolis, Dow AgroSciences. Derbi Report.

Sheets, J. J. and Storer, N. P. Analysis of Cry1Ac Binding to Proteins in Brush Border Membrane Vesicles of Corn Earworm Larvae (*Heleothis zea*). Interactions with Cry1F Proteins and Its Implication for Resistance in the Field. DAI-0417, 1-26. 2001. Indianapolis, Dow AgroSciences.

Tabashnik, B. E., Liu, Y. B., Finson, N., Masson, L., and Heckel, D. G. (1997). One gene in diamondback moth confers resistance to four *Bacillus thuringiensis* toxins. Proc. Natl. Acad. Sci. U.S. A 94, 1640-1644.

Tabashnik, B. E., Malvar, T., Liu, Y. B., Finson, N., Borthakur, D., Shin, B. S., Park, S. H., Masson, L., de Maagd, R. A., and Bosch, D. (1996). Cross-resistance of the diamondback moth indicates altered interactions with domain II of *Bacillus thuringiensis* toxins. Appl. Environ. Microbiol. 62, 2839-2844.

Tabashnik, B. E., Roush, R. T., Earle, E. D., and Shelton, A. M. (2000). Resistance to Bt toxins. Science 287, 42.

Wolfersberger, M. G. (1993). Preparation and partial characterization of amino acid transporting brush border membrane vesicles from the larval midgut of the gypsy moth (*Lymantria dispar*). Arch. Insect Biochem. Physiol 24, 139-147.

Xu, X., Yu, L., and Wu, Y. (2005). Disruption of a cadherin gene associated with resistance to Cry1Ac {delta}-endotoxin of *Bacillus thuringiensis* in *Helicoverpa armigera*. Appl Environ Microbiol 71, 948-954.

APPENDIX A

List of delta-endotoxins - from Crickmore et al. website (cited in application)
Accession Number is to NCBI entry

| Name | Acc No. | Authors | Year | Source Strain | Comment |
| --- | --- | --- | --- | --- | --- |
| Cry1Aa1 | AAA22353 | Schnepf et al | 1985 | Bt kurstaki HD1 | |
| Cry1Aa2 | AAA22552 | Shibano et al | 1985 | Bt sotto | |
| Cry1Aa3 | BAA00257 | Shimizu et al | 1988 | Bt aizawai IPL7 | |
| Cry1Aa4 | CAA31886 | Masson et al | 1989 | Bt entomocidus | |
| Cry1Aa5 | BAA04468 | Udayasuriyan et al | 1994 | Bt Fu-2-7 | |
| Cry1Aa6 | AAA86265 | Masson et al | 1994 | Bt kurstaki NRD-12 | |
| Cry1Aa7 | AAD46139 | Osman et al | 1999 | Bt C12 | |
| Cry1Aa8 | I26149 | Liu | 1996 | | DNA sequence only |
| Cry1Aa9 | BAA77213 | Nagamatsu et al | 1999 | Bt dendrolimus T84A1 | |
| Cry1Aa10 | AAD55382 | Hou and Chen | 1999 | Bt kurstaki HD-1-02 | |
| Cry1Aa11 | CAA70856 | Tounsi et al | 1999 | Bt kurstaki | |
| Cry1Aa12 | AAP80146 | Yao et al | 2001 | Bt Ly30 | |
| Cry1Aa13 | AAM44305 | Zhong et al | 2002 | Bt sotto | |
| Cry1Aa14 | AAP40639 | Ren et al | 2002 | unpublished | |
| Cry1Aa15 | AAY66993 | Sauka et al | 2005 | Bt INTA Mol-12 | |
| Cry1Ab1 | AAA22330 | Wabiko et al | 1986 | Bt berliner 1715 | |
| Cry1Ab2 | AAA22613 | Thorne et al | 1986 | Bt kurstaki | |
| Cry1Ab3 | AAA22561 | Geiser et al | 1986 | Bt kurstaki HD1 | |
| Cry1Ab4 | BAA00071 | Kondo et al | 1987 | Bt kurstaki HD1 | |
| Cry1Ab5 | CAA28405 | Hofte et al | 1986 | Bt berliner 1715 | |
| Cry1Ab6 | AAA22420 | Hefford et al | 1987 | Bt kurstaki NRD-12 | |
| Cry1Ab7 | CAA31620 | Haider & Ellar | 1988 | Bt aizawai IC1 | |
| Cry1Ab8 | AAA22551 | Oeda et al | 1987 | Bt aizawai IPL7 | |
| Cry1Ab9 | CAA38701 | Chak & Jen | 1993 | Bt aizawai HD133 | |
| Cry1Ab10 | A29125 | Fischhoff et al | 1987 | Bt kurstaki HD1 | |
| Cry1Ab11 | I12419 | Ely & Tippett | 1995 | Bt A20 | DNA sequence only |
| Cry1Ab12 | AAC64003 | Silva-Werneck et al | 1998 | Bt kurstaki S93 | |
| Cry1Ab13 | AAN76494 | Tan et al | 2002 | Bt c005 | |
| Cry1Ab14 | AAG16877 | Meza-Basso & Theoduloz | 2000 | Native Chilean Bt | |
| Cry1Ab15 | AAO13302 | Li et al | 2001 | Bt B-Hm-16 | |
| Cry1Ab16 | AAK55546 | Yu et al | 2002 | Bt AC-11 | |
| Cry1Ab17 | AAT46415 | Huang et al | 2004 | Bt WB9 | |
| Cry1Ab18 | AAQ88259 | Stobdan et al | 2004 | Bt | |
| Cry1Ab19 | AAW31761 | Zhong et al | 2005 | Bt X-2 | |
| Cry1Ab20 | ABB72460 | Liu et al | 2006 | BtC008 | |
| Cry1Ab21 | ABS18384 | Swiecicka et al | 2007 | Bt IS5056 | |
| Cry1Ab22 | ABW87320 | Wu and Feng | 2008 | BtS2491Ab | |

APPENDIX A-continued

List of delta-endotoxins - from Crickmore et al. website (cited in application)
Accession Number is to NCBI entry

| Name | Accession | Author | Year | Source | Notes |
|---|---|---|---|---|---|
| Cry1Ab-like | AAK14336 | Nagarathinam et al | 2001 | Bt kunthala RX24 | uncertain sequence |
| Cry1Ab-like | AAK14337 | Nagarathinam et al | 2001 | Bt kunthala RX28 | uncertain sequence |
| Cry1Ab-like | AAK14338 | Nagarathinam et al | 2001 | Bt kunthala RX27 | uncertain sequence |
| Cry1Ab-like | ABG88858 | Lin et al | 2006 | Bt ly4a3 | insufficient sequence |
| Cry1Ac1 | AAA22331 | Adang et al | 1985 | Bt kurstaki HD73 | |
| Cry1Ac2 | AAA22338 | Von Tersch et al | 1991 | Bt kenyae | |
| Cry1Ac3 | CAA38098 | Dardenne et al | 1990 | Bt BTS89A | |
| Cry1Ac4 | AAA73077 | Feitelson | 1991 | Bt kurstaki PS85A1 | |
| Cry1Ac5 | AAA22339 | Feitelson | 1992 | Bt kurstaki PS81GG | |
| Cry1Ac6 | AAA86266 | Masson et al | 1994 | Bt kurstaki NRD-12 | |
| Cry1Ac7 | AAB46989 | Herrera et al | 1994 | Bt kurstaki HD73 | |
| Cry1Ac8 | AAC44841 | Omolo et al | 1997 | Bt kurstaki HD73 | |
| Cry1Ac9 | AAB49768 | Gleave et al | 1992 | Bt DSIR732 | |
| Cry1Ac10 | CAA05505 | Sun | 1997 | Bt kurstaki YBT-1520 | |
| Cry1Ac11 | CAA10270 | Makhdoom & Riazuddin | 1998 | | |
| Cry1Ac12 | I12418 | Ely & Tippett | 1995 | Bt A20 | DNA sequence only |
| Cry1Ac13 | AAD38701 | Qiao et al | 1999 | Bt kurstaki HD1 | |
| Cry1Ac14 | AAQ06607 | Yao et al | 2002 | Bt Ly30 | |
| Cry1Ac15 | AAN07788 | Tzeng et al | 2001 | Bt from Taiwan | |
| Cry1Ac16 | AAU87037 | Zhao et al | 2005 | Bt H3 | |
| Cry1Ac17 | AAX18704 | Hire et al | 2005 | Bt kenyae HD549 | |
| Cry1Ac18 | AAY88347 | Kaur & Allam | 2005 | Bt SK-729 | |
| Cry1Ac19 | ABD37053 | Gao et al | 2005 | Bt C-33 | |
| Cry1Ac20 | ABB89046 | Tan et al | 2005 | | |
| Cry1Ac21 | AAY66992 | Sauka et al | 2005 | INTA Mol-12 | |
| Cry1Ac22 | ABZ01836 | Zhang & Fang | 2008 | Bt W015-1 | |
| Cry1Ac23 | CAQ30431 | Kashyap et al | 2008 | Bt | |
| Cry1Ac24 | ABL01535 | Arango et al | 2008 | Bt 146-158-01 | |
| Cry1Ac25 | FJ513324 | Guan Peng et al | 2008 | Bt Tm37-6 | No NCBI link July 09 |
| Cry1Ac26 | FJ617446 | Guan Peng et al | 2009 | Bt Tm41-4 | No NCBI link July 09 |
| Cry1Ac27 | FJ617447 | Guan Peng et al | 2009 | Bt Tm44-1B | No NCBI link July 09 |
| Cry1Ac28 | ACM90319 | Li et al | 2009 | Bt Q-12 | |
| Cry1Ad1 | AAA22340 | Feitelson | 1993 | Bt aizawai PS81I | |
| Cry1Ad2 | CAA01880 | Anonymous | 1995 | Bt PS81RR1 | |
| Cry1Ae1 | AAA22410 | Lee & Aronson | 1991 | Bt alesti | |
| Cry1Af1 | AAB82749 | Kang et al | 1997 | Bt NT0423 | |
| Cry1Ag1 | AAD46137 | Mustafa | 1999 | | |
| Cry1Ah1 | AAQ14326 | Tan et al | 2000 | | |
| Cry1Ah2 | ABB76664 | Qi et al | 2005 | Bt alesti | |
| Cry1Ai1 | AAO39719 | Wang et al | 2002 | | |
| Cry1A-like | AAK14339 | Nagarathinam et al | 2001 | Bt kunthala nags3 | uncertain sequence |
| Cry1Ba1 | CAA29898 | Brizzard & Whiteley | 1988 | Bt thuringiensis HD2 | |
| Cry1Ba2 | CAA65003 | Soetaert | 1996 | Bt entomocidus HD110 | |
| Cry1Ba3 | AAK63251 | Zhang et al | 2001 | | |
| Cry1Ba4 | AAK51084 | Nathan et al | 2001 | Bt entomocidus HD9 | |
| Cry1Ba5 | ABO20894 | Song et al | 2007 | Bt sfw-12 | |
| Cry1Ba6 | ABL60921 | Martins et al | 2006 | Bt S601 | |
| Cry1Bb1 | AAA22344 | Donovan et al | 1994 | Bt EG5847 | |
| Cry1Bc1 | CAA86568 | Bishop et al | 1994 | Bt morrisoni | |
| Cry1Bd1 | AAD10292 | Kuo et al | 2000 | Bt wuhanensis HD525 | |
| Cry1Bd2 | AAM93496 | Isakova et al | 2002 | Bt 834 | |
| Cry1Be1 | AAC32850 | Payne et al | 1998 | Bt PS158C2 | |
| Cry1Be2 | AAQ52387 | Baum et al | 2003 | | |
| Cry1Be3 | FJ716102 | Xiaodong Sun et al | 2009 | Bt | No NCBI link July 09 |
| Cry1Bf1 | CAC50778 | Arnaut et al | 2001 | | |
| Cry1Bf2 | AAQ52380 | Baum et al | 2003 | | |
| Cry1Bg1 | AAO39720 | Wang et al | 2002 | | |
| Cry1Ca1 | CAA30396 | Honee et al | 1988 | Bt entomocidus 60.5 | |
| Cry1Ca2 | CAA31951 | Sanchis et al | 1989 | Bt aizawai 7.29 | |
| Cry1Ca3 | AAA22343 | Feitelson | 1993 | Bt aizawai PS81I | |
| Cry1Ca4 | CAA01886 | Van Mellaert et al | 1990 | Bt entomocidus HD110 | |

APPENDIX A-continued

List of delta-endotoxins - from Crickmore et al. website (cited in application)
Accession Number is to NCBI entry

| Name | Accession | Author | Year | Strain | Notes |
|---|---|---|---|---|---|
| Cry1Ca5 | CAA65457 | Strizhov | 1996 | Bt aizawai 7.29 | |
| Cry1Ca6 | AAF37224 | Yu et al | 2000 | Bt AF-2 | |
| Cry1Ca7 | AAG50438 | Aixing et al | 2000 | Bt J8 | |
| Cry1Ca8 | AAM00264 | Chen et al | 2001 | Bt c002 | |
| Cry1Ca9 | AAL79362 | Kao et al | 2003 | Bt G10-01A | |
| Cry1Ca10 | AAN16462 | Lin et al | 2003 | Bt E05-20a | |
| Cry1Ca11 | AAX53094 | Cai et al | 2005 | Bt C-33 | |
| Cry1Cb1 | M97880 | Kalman et al | 1993 | Bt galleriae HD29 | DNA sequence only |
| Cry1Cb2 | AAG35409 | Song et al | 2000 | Bt c001 | |
| Cry1Cb3 | ACD50894 | Huang et al | 2008 | Bt 087 | |
| Cry1Cb-like | AAX63901 | Thammasittirong et al | 2005 | Bt TA476-1 | insufficient sequence |
| Cry1Da1 | CAA38099 | Hofte et al | 1990 | Bt aizawai HD68 | |
| Cry1Da2 | I76415 | Payne & Sick | 1997 | | DNA sequence only |
| Cry1Db1 | CAA80234 | Lambert | 1993 | Bt BTS00349A | |
| Cry1Db2 | AAK48937 | Li et al | 2001 | Bt B-Pr-88 | |
| Cry1Dc1 | ABK35074 | Lertwiriyawong et al | 2006 | Bt JC291 | |
| Cry1Ea1 | CAA37933 | Visser et al | 1990 | Bt kenyae 4F1 | |
| Cry1Ea2 | CAA39609 | Bosse et al | 1990 | Bt kenyae | |
| Cry1Ea3 | AAA22345 | Feitelson | 1991 | Bt kenyae PS81F | |
| Cry1Ea4 | AAD04732 | Barboza-Corona et al | 1998 | Bt kenyae LBIT-147 | |
| Cry1Ea5 | A15535 | Botterman et al | 1994 | | DNA sequence only |
| Cry1Ea6 | AAL50330 | Sun et al | 1999 | Bt YBT-032 | |
| Cry1Ea7 | AAW72936 | Huehne et al | 2005 | Bt JC190 | |
| Cry1Ea8 | ABX11258 | Huang et al | 2007 | Bt HZM2 | |
| Cry1Eb1 | AAA22346 | Feitelson | 1993 | Bt aizawai PS81A2 | |
| Cry1Fa1 | AAA22348 | Chambers et al | 1991 | Bt aizawai EG6346 | |
| Cry1Fa2 | AAA22347 | Feitelson | 1993 | Bt aizawai PS81I | |
| Cry1Fb1 | CAA80235 | Lambert | 1993 | Bt BTS00349A | |
| Cry1Fb2 | BAA25298 | Masuda & Asano | 1998 | Bt morrisoni INA67 | |
| Cry1Fb3 | AAF21767 | Song et al | 1998 | Bt morrisoni | |
| Cry1Fb4 | AAC10641 | Payne et al | 1997 | | |
| Cry1Fb5 | AAO13295 | Li et al | 2001 | Bt B-Pr-88 | |
| Cry1Fb6 | ACD50892 | Huang et al | 2008 | Bt 012 | |
| Cry1Fb7 | ACD50893 | Huang et al | 2008 | Bt 087 | |
| Cry1Ga1 | CAA80233 | Lambert | 1993 | Bt BTS0349A | |
| Cry1Ga2 | CAA70506 | Shevelev et al | 1997 | Bt wuhanensis | |
| Cry1Gb1 | AAD10291 | Kuo & Chak | 1999 | Bt wuhanensis HD525 | |
| Cry1Gb2 | AAO13756 | Li et al | 2000 | Bt B-Pr-88 | |
| Cry1Gc | AAQ52381 | Baum et al | 2003 | | |
| Cry1Ha1 | CAA80236 | Lambert | 1993 | Bt BTS02069AA | |
| Cry1Hb1 | AAA79694 | Koo et al | 1995 | Bt morrisoni BF190 | |
| Cry1H-like | AAF01213 | Srifah et al | 1999 | Bt JC291 | insufficient sequence |
| Cry1Ia1 | CAA44633 | Tailor et al | 1992 | Bt kurstaki | |
| Cry1Ia2 | AAA22354 | Gleave et al | 1993 | Bt kurstaki | |
| Cry1Ia3 | AAC36999 | Shin et al | 1995 | Bt kurstaki HD1 | |
| Cry1Ia4 | AAB00958 | Kostichka et al | 1996 | Bt AB88 | |
| Cry1Ia5 | CAA70124 | Selvapandiyan | 1996 | Bt 61 | |
| Cry1Ia6 | AAC26910 | Zhong et al | 1998 | Bt kurstaki S101 | |
| Cry1Ia7 | AAM73516 | Porcar et al | 2000 | Bt | |
| Cry1Ia8 | AAK66742 | Song et al | 2001 | | |
| Cry1Ia9 | AAQ08616 | Yao et al | 2002 | Bt Ly30 | |
| Cry1Ia10 | AAP86782 | Espindola et al | 2003 | Bt thuringiensis | |
| Cry1Ia11 | CAC85964 | Tounsi et al | 2003 | Bt kurstaki BNS3 | |
| Cry1Ia12 | AAV53390 | Grossi de Sa et al | 2005 | Bt | |
| Cry1Ia13 | ABF83202 | Martins et al | 2006 | Bt | |
| Cry1Ia14 | ACG63871 | Liu & Guo | 2008 | Bt11 | |
| Cry1Ia15 | FJ617445 | Guan Peng et al | 2009 | Bt E-1B | No NCBI link July 2009 |
| Cry1Ia16 | FJ617448 | Guan Peng et al | 2009 | Bt E-1A | No NCBI link July 2009 |
| Cry1Ib1 | AAA82114 | Shin et al | 1995 | Bt entomocidus BP465 | |
| Cry1Ib2 | ABW88019 | Guan et al | 2007 | Bt PP61 | |
| Cry1Ib3 | ACD75515 | Liu & Guo | 2008 | Bt GS8 | |
| Cry1Ic1 | AAC62933 | Osman et al | 1998 | Bt C18 | |
| Cry1Ic2 | AAE71691 | Osman et al | 2001 | | |
| Cry1Id1 | AAD44366 | Choi | 2000 | | |
| Cry1Ie1 | AAG43526 | Song et al | 2000 | Bt BTC007 | |
| Cry1If1 | AAQ52382 | Baum et al | 2003 | | |

APPENDIX A-continued

List of delta-endotoxins - from Crickmore et al. website (cited in application)
Accession Number is to NCBI entry

| | | | | | |
|---|---|---|---|---|---|
| Cry1I-like | AAC31094 | Payne et al | 1998 | | insufficient sequence |
| Cry1I-like | ABG88859 | Lin & Fang | 2006 | Bt ly4a3 | insufficient sequence |
| Cry1Ja1 | AAA22341 | Donovan | 1994 | Bt EG5847 | |
| Cry1Jb1 | AAA98959 | Von Tersch & Gonzalez | 1994 | Bt EG5092 | |
| Cry1Jc1 | AAC31092 | Payne et al | 1998 | | |
| Cry1Jc2 | AAQ52372 | Baum et al | 2003 | | |
| Cry1Jd1 | CAC50779 | Arnaut et al | 2001 | Bt | |
| Cry1Ka1 | AAB00376 | Koo et al | 1995 | Bt morrisoni BF190 | |
| Cry1La1 | AAS60191 | Je et al | 2004 | Bt kurstaki K1 | |
| Cry1-like | AAC31091 | Payne et al | 1998 | | insufficient sequence |
| Cry2Aa1 | AAA22335 | Donovan et al | 1989 | Bt kurstaki | |
| Cry2Aa2 | AAA83516 | Widner & Whiteley | 1989 | Bt kurstaki HD1 | |
| Cry2Aa3 | D86064 | Sasaki et al | 1997 | Bt sotto | DNA sequence only |
| Cry2Aa4 | AAC04867 | Misra et al | 1998 | Bt kenyae HD549 | |
| Cry2Aa5 | CAA10671 | Yu & Pang | 1999 | Bt SL39 | |
| Cry2Aa6 | CAA10672 | Yu & Pang | 1999 | Bt YZ71 | |
| Cry2Aa7 | CAA10670 | Yu & Pang | 1999 | Bt CY29 | |
| Cry2Aa8 | AAO13734 | Wei et al | 2000 | Bt Dongbei 66 | |
| Cry2Aa9 | AAO13750 | Zhang et al | 2000 | | |
| Cry2Aa10 | AAQ04263 | Yao et al | 2001 | | |
| Cry2Aa11 | AAQ52384 | Baum et al | 2003 | | |
| Cry2Aa12 | ABI83671 | Tan et al | 2006 | Bt Rpp39 | |
| Cry2Aa13 | ABL01536 | Arango et al | 2008 | Bt 146-158-01 | |
| Cry2Aa14 | ACF04939 | Hire et al | 2008 | Bt HD-550 | |
| Cry2Ab1 | AAA22342 | Widner & Whiteley | 1989 | Bt kurstaki HD1 | |
| Cry2Ab2 | CAA39075 | Dankocsik et al | 1990 | Bt kurstaki HD1 | |
| Cry2Ab3 | AAG36762 | Chen et al | 1999 | Bt BTC002 | |
| Cry2Ab4 | AAO13296 | Li et al | 2001 | Bt B-Pr-88 | |
| Cry2Ab5 | AAQ04609 | Yao et al | 2001 | Bt ly30 | |
| Cry2Ab6 | AAP59457 | Wang et al | 2003 | Bt WZ-7 | |
| Cry2Ab7 | AAZ66347 | Udayasuriyan et al | 2005 | Bt 14-1 | |
| Cry2Ab8 | ABC95996 | Huang et al | 2006 | Bt WB2 | |
| Cry2Ab9 | ABC74968 | Zhang et al | 2005 | Bt LLB6 | |
| Cry2Ab10 | EF157306 | Lin et al | 2006 | Bt LyD | |
| Cry2Ab11 | CAM84575 | Saleem et al | 2007 | Bt CMBL-BT1 | |
| Cry2Ab12 | ABM21764 | Lin et al | 2007 | Bt LyD | |
| Cry2Ab13 | ACG76120 | Zhu et al | 2008 | Bt ywc5-4 | |
| Cry2Ab14 | ACG76121 | Zhu et al | 2008 | Bt Bts | |
| Cry2Ac1 | CAA40536 | Aronson | 1991 | Bt shanghai S1 | |
| Cry2Ac2 | AAG35410 | Song et al | 2000 | | |
| Cry2Ac3 | AAQ52385 | Baum et al | 2003 | | |
| Cry2Ac4 | ABC95997 | Huang et al | 2006 | Bt WB9 | |
| Cry2Ac5 | ABC74969 | Zhang et al | 2005 | | |
| Cry2Ac6 | ABC74793 | Xia et al | 2006 | Bt wuhanensis | |
| Cry2Ac7 | CAL18690 | Saleem et al | 2008 | Bt SBSBT-1 | |
| Cry2Ac8 | CAM09325 | Saleem et al | 2007 | Bt CMBL-BT1 | |
| Cry2Ac9 | CAM09326 | Saleem et al | 2007 | Bt CMBL-BT2 | |
| Cry2Ac10 | ABN15104 | Bai et al | 2007 | Bt QCL-1 | |
| Cry2Ac11 | CAM83895 | Saleem et al | 2007 | Bt HD29 | |
| Cry2Ac12 | CAM83896 | Saleem et al | 2007 | Bt CMBL-BT3 | |
| Cry2Ad1 | AAF09583 | Choi et al | 1999 | Bt BR30 | |
| Cry2Ad2 | ABC86927 | Huang et al | 2006 | Bt WB10 | |
| Cry2Ad3 | CAK29504 | Saleem et al | 2006 | Bt 5_2AcT(1) | |
| Cry2Ad4 | CAM32331 | Saleem et al | 2007 | Bt CMBL-BT2 | |
| Cry2Ad5 | CAO78739 | Saleem et al | 2007 | Bt HD29 | |
| Cry2Ae1 | AAQ52362 | Baum et al | 2003 | | |
| Cry2Af1 | ABO30519 | Beard et al | 2007 | Bt C81 | |
| Cry2Ag | ACH91610 | Zhu et al | 2008 | Bt JF19-2 | |
| Cry2Ah | EU939453 | Zhang et al | 2008 | Bt | No NCBI link July 09 |
| Cry2Ah2 | ACL80665 | Zhang et al | 2009 | Bt BRC-ZQL3 | |
| Cry2Ai | FJ788388 | Udayasuriyan et al | 2009 | Bt | No NCBI link July 09 |
| Cry3Aa1 | AAA22336 | Herrnstadt et al | 1987 | Bt san diego | |
| Cry3Aa2 | AAA22541 | Sekar et al | 1987 | Bt tenebrionis | |
| Cry3Aa3 | CAA68482 | Hofte et al | 1987 | | |
| Cry3Aa4 | AAA22542 | McPherson et al | 1988 | Bt tenebrionis | |
| Cry3Aa5 | AAA50255 | Donovan et al | 1988 | Bt morrisoni EG2158 | |
| Cry3Aa6 | AAC43266 | Adams et al | 1994 | Bt tenebrionis | |
| Cry3Aa7 | CAB41411 | Zhang et al | 1999 | Bt 22 | |
| Cry3Aa8 | AAS79487 | Gao and Cai | 2004 | Bt YM-03 | |
| Cry3Aa9 | AAW05659 | Bulla and Candas | 2004 | Bt UTD-001 | |
| Cry3Aa10 | AAU29411 | Chen et al | 2004 | Bt 886 | |
| Cry3Aa11 | AAW82872 | Kurt et al | 2005 | Bt tenebrionis Mm2 | |

APPENDIX A-continued

List of delta-endotoxins - from Crickmore et al. website (cited in application)
Accession Number is to NCBI entry

| Name | Accession | Authors | Year | Strain | Notes |
|---|---|---|---|---|---|
| Cry3Aa12 | ABY49136 | Sezen et al | 2008 | Bt tenebrionis | |
| Cry3Ba1 | CAA34983 | Sick et al | 1990 | Bt tolworthi 43F | |
| Cry3Ba2 | CAA00645 | Peferoen et al | 1990 | Bt PGSI208 | |
| Cry3Bb1 | AAA22334 | Donovan et al | 1992 | Bt EG4961 | |
| Cry3Bb2 | AAA74198 | Donovan et al | 1995 | Bt EG5144 | |
| Cry3Bb3 | I15475 | Peferoen et al | 1995 | | DNA sequence only |
| Cry3Ca1 | CAA42469 | Lambert et al | 1992 | Bt kurstaki BtI109P | |
| Cry4Aa1 | CAA68485 | Ward & Ellar | 1987 | Bt israelensis | |
| Cry4Aa2 | BAA00179 | Sen et al | 1988 | Bt israelensis HD522 | |
| Cry4Aa3 | CAD30148 | Berry et al | 2002 | Bt israelensis | |
| Cry4A-like | AAY96321 | Mahalakshmi et al | 2005 | Bt LDC-9 | insufficient sequence |
| Cry4Ba1 | CAA30312 | Chungjatpornchai et al | 1988 | Bt israelensis 4Q2-72 | |
| Cry4Ba2 | CAA30114 | Tungpradubkul et al | 1988 | Bt israelensis | |
| Cry4Ba3 | AAA22337 | Yamamoto et al | 1988 | Bt israelensis | |
| Cry4Ba4 | BAA00178 | Sen et al | 1988 | Bt israelensis HD522 | |
| Cry4Ba5 | CAD30095 | Berry et al | 2002 | Bt israelensis | |
| Cry4Ba-like | ABC47686 | Mahalakshmi et al | 2005 | Bt LDC-9 | insufficient sequence |
| Cry4Ca1 | EU646202 | Shu et al | 2008 | | No NCBI link July 09 |
| Cry4Cb1 | FJ403208 | Jun & Furong | 2008 | Bt HS18-1 | No NCBI link July 09 |
| Cry4Cb2 | FJ597622 | Jun & Furong | 2008 | Bt Ywc2-8 | No NCBI link July 09 |
| Cry4Cc1 | FJ403207 | Jun & Furong | 2008 | Bt MC28 | No NCBI link July 09 |
| Cry5Aa1 | AAA67694 | Narva et al | 1994 | Bt darmstadiensis PS17 | |
| Cry5Ab1 | AAA67693 | Narva et al | 1991 | Bt darmstadiensis PS17 | |
| Cry5Ac1 | I34543 | Payne et al | 1997 | | DNA sequence only |
| Cry5Ad1 | ABQ82087 | Lenane et al | 2007 | Bt L366 | |
| Cry5Ba1 | AAA68598 | Foncerrada & Narva | 1997 | Bt PS86Q3 | |
| Cry5Ba2 | ABW88932 | Guo et al | 2008 | YBT 1518 | |
| Cry6Aa1 | AAA22357 | Narva et al | 1993 | Bt PS52A1 | |
| Cry6Aa2 | AAM46849 | Bai et al | 2001 | YBT 1518 | |
| Cry6Aa3 | ABH03377 | Jia et al | 2006 | Bt 96418 | |
| Cry6Ba1 | AAA22358 | Narva et al | 1991 | Bt PS69D1 | |
| Cry7Aa1 | AAA22351 | Lambert et al | 1992 | Bt galleriae PGSI245 | |
| Cry7Ab1 | AAA21120 | Narva & Fu | 1994 | Bt dakota HD511 | |
| Cry7Ab2 | AAA21121 | Narva & Fu | 1994 | Bt kumamotoensis 867 | |
| Cry7Ab3 | ABX24522 | Song et al | 2008 | Bt WZ-9 | |
| Cry7Ab4 | EU380678 | Shu et al | 2008 | Bt | No NCBI link July 09 |
| Cry7Ab5 | ABX79555 | Aguirre-Arzola et al | 2008 | Bt monterrey GM-33 | |
| Cry7Ab6 | ACI44005 | Deng et al | 2008 | Bt HQ122 | |
| Cry7Ab7 | FJ940776 | Wang et al | 2009 | | No NCBI link Sept 09 |
| Cry7Ab8 | GU145299 | Feng Jing | 2009 | | No NCBI link Nov 09 |
| Cry7Ba1 | ABB70817 | Zhang et al | 2006 | Bt huazhongensis | |
| Cry7Ca1 | ABR67863 | Gao et al | 2007 | Bt BTH-13 | |
| Cry7Da1 | ACQ99547 | Yi et al | 2009 | Bt LH-2 | |
| Cry8Aa1 | AAA21117 | Narva & Fu | 1992 | Bt kumamotoensis | |
| Cry8Ab1 | EU044830 | Cheng et al | 2007 | Bt B-JJX | No NCBI link July 09 |
| Cry8Ba1 | AAA21118 | Narva & Fu | 1993 | Bt kumamotoensis | |
| Cry8Bb1 | CAD57542 | Abad et al | 2002 | | |
| Cry8Bc1 | CAD57543 | Abad et al | 2002 | | |
| Cry8Ca1 | AAA21119 | Sato et al. | 1995 | Bt japonensis Buibui | |
| Cry8Ca2 | AAR98783 | Shu et al | 2004 | Bt HBF-1 | |
| Cry8Ca3 | EU625349 | Du et al | 2008 | Bt FTL-23 | No NCBI link July 09 |
| Cry8Da1 | BAC07226 | Asano et al | 2002 | Bt galleriae | |
| Cry8Da2 | BD133574 | Asano et al | 2002 | Bt | DNA sequence only |
| Cry8Da3 | BD133575 | Asano et al | 2002 | Bt | DNA sequence only |
| Cry8Db1 | BAF93483 | Yamaguchi et al | 2007 | Bt BBT2-5 | |
| Cry8Ea1 | AAQ73470 | Fuping et al | 2003 | Bt 185 | |
| Cry8Ea2 | EU047597 | Liu et al | 2007 | Bt B-DLL | No NCBI link July 09 |
| Cry8Fa1 | AAT48690 | Shu et al | 2004 | Bt 185 | also AAW81032 |
| Cry8Ga1 | AAT46073 | Shu et al | 2004 | Bt HBF-18 | |
| Cry8Ga2 | ABC42043 | Yan et al | 2008 | Bt 145 | |
| Cry8Ga3 | FJ198072 | Xiaodong et al | 2008 | Bt FCD114 | No NCBI link July 09 |
| Cry8Ha1 | EF465532 | Fuping et al | 2006 | Bt 185 | No NCBI link July 09 |
| Cry8Ia1 | EU381044 | Yan et al | 2008 | Bt su4 | No NCBI link July 09 |
| Cry8Ja1 | EU625348 | Du et al | 2008 | Bt FPT-2 | No NCBI link July 09 |
| Cry8Ka1 | FJ422558 | Quezado et al | 2008 | | No NCBI link July 09 |

APPENDIX A-continued

List of delta-endotoxins - from Crickmore et al. website (cited in application)
Accession Number is to NCBI entry

| Name | Accession | Authors | Year | Source | Notes |
|---|---|---|---|---|---|
| Cry8Ka2 | ACN87262 | Noguera & Ibarra | 2009 | Bt kenyae | |
| Cry8-like | FJ770571 | Noguera & Ibarra | 2009 | Bt canadensis | DNA sequence only |
| Cry8-like | ABS53003 | Mangena et al | 2007 | Bt | |
| Cry9Aa1 | CAA41122 | Shevelev et al | 1991 | Bt galleriae | |
| Cry9Aa2 | CAA41425 | Gleave et al | 1992 | Bt DSIR517 | |
| Cry9Aa3 | GQ249293 | Su et al | 2009 | Bt SC5(D2) | No NCBI link July 09 |
| Cry9Aa4 | GQ249294 | Su et al | 2009 | Bt T03C001 | No NCBI link July 09 |
| Cry9Aa like | AAQ52376 | Baum et al | 2003 | | incomplete sequence |
| Cry9Ba1 | CAA52927 | Shevelev et al | 1993 | Bt galleriae | |
| Cry9Bb1 | AAV28716 | Silva-Werneck et al | 2004 | Bt japonensis | |
| Cry9Ca1 | CAA85764 | Lambert et al | 1996 | Bt tolworthi | |
| Cry9Ca2 | AAQ52375 | Baum et al | 2003 | | |
| Cry9Da1 | BAA19948 | Asano | 1997 | Bt japonensis N141 | |
| Cry9Da2 | AAB97923 | Wasano & Ohba | 1998 | Bt japonensis | |
| Cry9Da3 | GQ249295 | Su et al | 2009 | Bt T03B001 | No NCBI link July 09 |
| Cry9Da4 | GQ249297 | Su et al | 2009 | Bt T03B001 | No NCBI link July 09 |
| Cry9Db1 | AAX78439 | Flannagan & Abad | 2005 | Bt kurstaki DP1019 | |
| Cry9Ea1 | BAA34908 | Midoh & Oyama | 1998 | Bt aizawai SSK-10 | |
| Cry9Ea2 | AAO12908 | Li et al | 2001 | Bt B-Hm-16 | |
| Cry9Ea3 | ABM21765 | Lin et al | 2006 | Bt lyA | |
| Cry9Ea4 | ACE88267 | Zhu et al | 2008 | Bt ywc5-4 | |
| Cry9Ea5 | ACF04743 | Zhu et al | 2008 | Bts | |
| Cry9Ea6 | ACG63872 | Liu & Guo | 2008 | Bt 11 | |
| Cry9Ea7 | FJ380927 | Sun et al | 2008 | | No NCBI link July 09 |
| Cry9Ea8 | GQ249292 | Su et al | 2009 | GQ249292 | No NCBI link July 09 |
| Cry9Eb1 | CAC50780 | Arnaut et al | 2001 | | |
| Cry9Eb2 | GQ249298 | Su et al | 2009 | Bt T03B001 | No NCBI link July 09 |
| Cry9Ec1 | AAC63366 | Wasano et al | 2003 | Bt galleriae | |
| Cry9Ed1 | AAX78440 | Flannagan & Abad | 2005 | Bt kurstaki DP1019 | |
| Cry9Ee1 | GQ249296 | Su et al | 2009 | Bt T03B001 | No NCBI link Aug 09 |
| Cry9-like | AAC63366 | Wasano et al | 1998 | Bt galleriae | insufficient sequence |
| Cry10Aa1 | AAA22614 | Thorne et al | 1986 | Bt israelensis | |
| Cry10Aa2 | E00614 | Aran & Toomasu | 1996 | Bt israelensis ONR-60A | DNA sequence only |
| Cry10Aa3 | CAD30098 | Berry et al | 2002 | Bt israelensis | |
| Cry10A-like | DQ167578 | Mahalakshmi et al | 2006 | Bt LDC-9 | incomplete sequence |
| Cry11Aa1 | AAA22352 | Donovan et al | 1988 | Bt israelensis | |
| Cry11Aa2 | AAA22611 | Adams et al | 1989 | Bt israelensis | |
| Cry11Aa3 | CAD30081 | Berry et al | 2002 | Bt israelensis | |
| Cry11Aa-like | DQ166531 | Mahalakshmi et al | 2007 | Bt LDC-9 | incomplete sequence |
| Cry11Ba1 | CAA60504 | Delecluse et al | 1995 | Bt jegathesan 367 | |
| Cry11Bb1 | AAC97162 | Orduz et al | 1998 | Bt medellin | |
| Cry12Aa1 | AAA22355 | Narva et al | 1991 | Bt PS33F2 | |
| Cry13Aa1 | AAA22356 | Narva et al | 1992 | Bt PS63B | |
| Cry14Aa1 | AAA21516 | Narva et al | 1994 | Bt sotto PS80JJ1 | |
| Cry15Aa1 | AAA22333 | Brown & Whiteley | 1992 | Bt thompsoni | |
| Cry16Aa1 | CAA63860 | Barloy et al | 1996 | Cb malaysia CH18 | |
| Cry17Aa1 | CAA67841 | Barloy et al | 1998 | Cb malaysia CH18 | |
| Cry18Aa1 | CAA67506 | Zhang et al | 1997 | Paenibacillus popilliae | |
| Cry18Ba1 | AAF89667 | Patel et al | 1999 | Paenibacillus popilliae | |
| Cry18Ca1 | AAF89668 | Patel et al | 1999 | Paenibacillus popilliae | |
| Cry19Aa1 | CAA68875 | Rosso & Delecluse | 1996 | Bt jegathesan 367 | |
| Cry19Ba1 | BAA32397 | Hwang et al | 1998 | Bt higo | |
| Cry20Aa1 | AAB93476 | Lee & Gill | 1997 | Bt fukuokaensis | |
| Cry20Ba1 | ACS93601 | Noguera & Ibarra | 2009 | Bt higo LBIT-976 | |
| Cry20-like | GQ144333 | Yi et al | 2009 | Bt Y-5 | DNA sequence only |
| Cry21Aa1 | I32932 | Payne et al | 1996 | | DNA sequence only |
| Cry21Aa2 | I66477 | Feitelson | 1997 | | DNA sequence only |
| Cry21Ba1 | BAC06484 | Sato & Asano | 2002 | Bt roskildiensis | |
| Cry22Aa1 | I34547 | Payne et al | 1997 | | DNA sequence only |
| Cry22Aa2 | CAD43579 | Isaac et al | 2002 | Bt | |
| Cry22Aa3 | ACD93211 | Du et al | 2008 | Bt FZ-4 | |
| Cry22Ab1 | AAK50456 | Baum et al | 2000 | Bt EG4140 | |
| Cry22Ab2 | CAD43577 | Isaac et al | 2002 | Bt | |
| Cry22Ba1 | CAD43578 | Isaac et al | 2002 | Bt | |
| Cry23Aa1 | AAF76375 | Donovan et al | 2000 | Bt | Binary with Cry37Aa1 |
| Cry24Aa1 | AAC61891 | Kawalek and Gill | 1998 | Bt jegathesan | |

APPENDIX A-continued

List of delta-endotoxins - from Crickmore et al. website (cited in application)
Accession Number is to NCBI entry

| Name | Accession | Authors | Year | Strain | Notes |
|---|---|---|---|---|---|
| Cry24Ba1 | BAD32657 | Ohgushi et al | 2004 | Bt sotto | |
| Cry24Ca1 | CAJ43600 | Beron & Salerno | 2005 | Bt FCC-41 | |
| Cry25Aa1 | AAC61892 | Kawalek and Gill | 1998 | Bt jegathesan | |
| Cry26Aa1 | AAD25075 | Wojciechowska et al | 1999 | Bt finitimus B-1166 | |
| Cry27Aa1 | BAA82796 | Saitoh | 1999 | Bt higo | |
| Cry28Aa1 | AAD24189 | Wojciechowska et al | 1999 | Bt finitimus B-1161 | |
| Cry28Aa2 | AAG00235 | Moore and Debro | 2000 | Bt finitimus | |
| Cry29Aa1 | CAC80985 | Delecluse et al | 2000 | Bt medellin | |
| Cry30Aa1 | CAC80986 | Delecluse et al | 2000 | Bt medellin | |
| Cry30Ba1 | BAD00052 | Ito et al | 2003 | Bt entomocidus | |
| Cry30Ca1 | BAD67157 | Ohgushi et al | 2004 | Bt sotto | |
| Cry30Ca2 | ACU24781 | Sun and Park | 2009 | Bt jegathesan 367 | |
| Cry30Da1 | EF095955 | Shu et al | 2006 | Bt Y41 | No NCBI link July09 |
| Cry30Db1 | BAE80088 | Kishida et al | 2006 | Bt aizawai BUN1-14 | |
| Cry30Ea1 | ACC95445 | Fang et al | 2007 | Bt S2160-1 | |
| Cry30Ea2 | FJ499389 | Jun et al | 2008 | Bt Ywc2-8 | No NCBI link July09 |
| Cry30Fa1 | ACI22625 | Tan et al | 2008 | Bt MC28 | |
| Cry30Ga1 | ACG60020 | Zhu et al | 2008 | Bt HS18-1 | |
| Cry31Aa1 | BAB11757 | Saitoh & Mizuki | 2000 | Bt 84-HS-1-11 | |
| Cry31Aa2 | AAL87458 | Jung and Cote | 2000 | Bt M15 | |
| Cry31Aa3 | BAE79808 | Uemori et al | 2006 | Bt B0195 | |
| Cry31Aa4 | BAF32571 | Yasutake et al | 2006 | Bt 79-25 | |
| Cry31Aa5 | BAF32572 | Yasutake et al | 2006 | Bt 92-10 | |
| Cry31Ab1 | BAE79809 | Uemori et al | 2006 | Bt B0195 | |
| Cry31Ab2 | BAF32570 | Yasutake et al | 2006 | Bt 31-5 | |
| Cry31Ac1 | BAF34368 | Yasutake et al | 2006 | Bt 87-29 | |
| Cry32Aa1 | AAG36711 | Balasubramanian et al | 2001 | Bt yunnanensis | |
| Cry32Ba1 | BAB78601 | Takebe et al | 2001 | Bt | |
| Cry32Ca1 | BAB78602 | Takebe et al | 2001 | Bt | |
| Cry32Da1 | BAB78603 | Takebe et al | 2001 | Bt | |
| Cry33Aa1 | AAL26871 | Kim et al | 2001 | Bt dakota | |
| Cry34Aa1 | AAG50341 | Ellis et al | 2001 | Bt PS80JJ1 | Binary with Cry35Aa1 |
| Cry34Aa2 | AAK64560 | Rupar et al | 2001 | Bt EG5899 | Binary with Cry35Aa2 |
| Cry34Aa3 | AAT29032 | Schnepf et al | 2004 | Bt PS69Q | Binary with Cry35Aa3 |
| Cry34Aa4 | AAT29030 | Schnepf et al | 2004 | Bt PS185GG | Binary with Cry35Aa4 |
| Cry34Ab1 | AAG41671 | Moellenbeck et al | 2001 | Bt PS149B1 | Binary with Cry35Ab1 |
| Cry34Ac1 | AAG50118 | Ellis et al | 2001 | Bt PS167H2 | Binary with Cry35Ac1 |
| Cry34Ac2 | AAK64562 | Rupar et al | 2001 | Bt EG9444 | Binary with Cry35Ab2 |
| Cry34Ac3 | AAT29029 | Schnepf et al | 2004 | Bt KR1369 | Binary with Cry35Ab3 |
| Cry34Ba1 | AAK64565 | Rupar et al | 2001 | Bt EG4851 | Binary with Cry35Ba1 |
| Cry34Ba2 | AAT29033 | Schnepf et al | 2004 | Bt PS201L3 | Binary with Cry35Ba2 |
| Cry34Ba3 | AAT29031 | Schnepf et al | 2004 | Bt PS201HH2 | Binary with Cry35Ba3 |
| Cry35Aa1 | AAG50342 | Ellis et al | 2001 | Bt PS80JJ1 | Binary with Cry34Aa1 |
| Cry35Aa2 | AAK64561 | Rupar et al | 2001 | Bt EG5899 | Binary with Cry34Aa2 |
| Cry35Aa3 | AAT29028 | Schnepf et al | 2004 | Bt PS69Q | Binary with Cry34Aa3 |
| Cry35Aa4 | AAT29025 | Schnepf et al | 2004 | Bt PS185GG | Binary with Cry34Aa4 |
| Cry35Ab1 | AAG41672 | Moellenbeck et al | 2001 | Bt PS149B1 | Binary with Cry34Ab1 |
| Cry35Ab2 | AAK64563 | Rupar et al | 2001 | Bt EG9444 | Binary with Cry34Ac2 |
| Cry35Ab3 | AY536891 | AAT29024 | 2004 | Bt KR1369 | Binary with Cry34Ab3 |
| Cry35Ac1 | AAG50117 | Ellis et al | 2001 | Bt PS167H2 | Binary with Cry34Ac1 |
| Cry35Ba1 | AAK64566 | Rupar et al | 2001 | Bt EG4851 | Binary with Cry34Ba1 |
| Cry35Ba2 | AAT29027 | Schnepf et al | 2004 | Bt PS201L3 | Binary with Cry34Ba2 |
| Cry35Ba3 | AAT29026 | Schnepf et al | 2004 | Bt PS201HH2 | Binary with Cry34Ba3 |
| Cry36Aa1 | AAK64558 | Rupar et al | 2001 | Bt | |
| Cry37Aa1 | AAF76376 | Donovan et al | 2000 | Bt | Binary with Cry23Aa |
| Cry38Aa1 | AAK64559 | Rupar et al | 2000 | Bt | |
| Cry39Aa1 | BAB72016 | Ito et al | 2001 | Bt aizawai | |
| Cry40Aa1 | BAB72018 | Ito et al | 2001 | Bt aizawai | |
| Cry40Ba1 | BAC77648 | Ito et al | 2003 | Bun1-14 | |
| Cry40Ca1 | EU381045 | Shu et al | 2008 | Bt Y41 | No NCBI link July09 |
| Cry40Da1 | ACF15199 | Zhang et al | 2008 | Bt S2096-2 | |
| Cry41Aa1 | BAD35157 | Yamashita et al | 2003 | Bt A1462 | |
| Cry41Ab1 | BAD35163 | Yamashita et al | 2003 | Bt A1462 | |
| Cry42Aa1 | BAD35166 | Yamashita et al | 2003 | Bt A1462 | |
| Cry43Aa1 | BAD15301 | Yokoyama and Tanaka | 2003 | P. lentimorbus semadara | |
| Cry43Aa2 | BAD95474 | Nozawa | 2004 | P. popilliae popilliae | |
| Cry43Ba1 | BAD15303 | Yokoyama and Tanaka | 2003 | P. lentimorbus semadara | |
| Cry43-like | BAD15305 | Yokoyama and Tanaka | 2003 | P. lentimorbus semadara | |

APPENDIX A-continued

List of delta-endotoxins - from Crickmore et al. website (cited in application)
Accession Number is to NCBI entry

| | | | | | | | |
|---|---|---|---|---|---|---|---|
| Cry44Aa | | BAD08532 | Ito et al | 2004 | Bt entomocidus INA288 | | |
| Cry45Aa | | BAD22577 | Okumura et al | 2004 | Bt 89-T-34-22 | | |
| Cry46Aa | | BAC79010 | Ito et al | 2004 | Bt dakota | | |
| Cry46Aa2 | | BAG68906 | Ishikawa et al | 2008 | Bt A1470 | | |
| Cry46Ab | | BAD35170 | Yamagiwa et al | 2004 | Bt | | |
| Cry47Aa | | AAY24695 | Kongsuwan et al | 2005 | Bt CAA890 | | |
| Cry48Aa | | CAJ18351 | Jones and Berry | 2005 | Bs IAB59 | binary with 49Aa | |
| Cry48Aa2 | | CAJ86545 | Jones and Berry | 2006 | Bs 47-6B | binary with 49Aa2 | |
| Cry48Aa3 | | CAJ86546 | Jones and Berry | 2006 | Bs NHA15b | binary with 49Aa3 | |
| Cry48Ab | | CAJ86548 | Jones and Berry | 2006 | Bs LP1G | binary with 49Ab1 | |
| Cry48Ab2 | | CAJ86549 | Jones and Berry | 2006 | Bs 2173 | binary with 49Aa4 | |
| Cry49Aa | | CAH56541 | Jones and Berry | 2005 | Bs IAB59 | binary with 48Aa | |
| Cry49Aa2 | | CAJ86541 | Jones and Berry | 2006 | Bs 47-6B | binary with 48Aa2 | |
| Cry49Aa3 | | CAJ86543 | Jones and Berry | 2006 | BsNHA15b | binary with 48Aa3 | |
| Cry49Aa4 | | CAJ86544 | Jones and Berry | 2006 | Bs 2173 | binary with 48Ab2 | |
| Cry49Ab1 | | CAJ86542 | Jones and Berry | 2006 | Bs LP1G | binary with 48Ab1 | |
| Cry50Aa1 | | BAE86999 | Ohgushi et al | 2006 | Bt sotto | | |
| Cry51Aa1 | | ABI14444 | Meng et al | 2006 | Bt F14-1 | | |
| Cry52Aa1 | | EF613489 | Song et al | 2007 | Bt Y41 | No NCBI link July09 | |
| Cry52Ba1 | | FJ361760 | Jun et al | 2008 | Bt BM59-2 | No NCBI link July09 | |
| Cry53Aa1 | | EF633476 | Song et al | 2007 | Bt Y41 | No NCBI link July09 | |
| Cry53Ab1 | | FJ361759 | Jun et al | 2008 | Bt MC28 | No NCBI link July09 | |
| Cry54Aa1 | | ACA52194 | Tan et al | 2009 | Bt MC28 | | |
| Cry55Aa1 | | ABW88931 | Guo et al | 2008 | YBT 1518 | | |
| Cry55Aa2 | | AAE33526 | Bradfisch et al | 2000 | BT Y41 | | |
| Cry56Aa1 | | FJ597621 | Jun & Furong | 2008 | Bt Ywc2-8 | No NCBI link July09 | |
| Cry56Aa2 | | GQ483512 | Guan Peng et al | 2009 | Bt G7-1 | No NCBI link Aug09 | |
| Cry57Aa1 | | ANC87261 | Noguera & Ibarra | 2009 | Bt kim | | |
| Cry58Aa1 | | ANC87260 | Noguera & Ibarra | 2009 | Bt entomocidus | | |
| Cry59Aa1 | | ACR43758 | Noguera & Ibarra | 2009 | Bt kim LBIT-980 | | |
| Vip3Aa1 | Vip3Aa | AAC37036 | Estruch et al | 1996 | PNAS 93, 5389-5394 | AB88 | |
| Vip3Aa2 | Vip3Ab | AAC37037 | Estruch et al | 1996 | PNAS 93, 5389-5394 | AB424 | |
| Vip3Aa3 | Vip3Ac | | Estruch et al | 2000 | U.S. Pat. No. 6,137,033 October 2000 | | |
| Vip3Aa4 | PS36A Sup | AAR81079 | Feitelson et al | 1998 | U.S. Pat. No. 6,656,908 December 2003 | Bt PS36A | WO9818932(A2, A3) 7 May 1998 |
| Vip3Aa5 | PS81F Sup | AAR81080 | Feitelson et al | 1998 | U.S. Pat. No. 6,656,908 December 2003 | Bt PS81F | WO9818932(A2, A3) 7 May 1998 |
| Vip3Aa6 | Jav90 Sup | AAR81081 | Feitelson et al | 1998 | U.S. Pat. No. 6,656,908 December 2003 | Bt | WO9818932(A2, A3) 7 May 1998 |
| Vip3Aa7 | Vip83 | AAK95326 | Cai et al | 2001 | unpublished | Bt YBT-833 | |
| Vip3Aa8 | Vip3A | AAK97481 | Loguercio et al | 2001 | unpublished | Bt HD125 | |
| Vip3Aa9 | VipS | CAA76665 | Selvapandiyan et al | 2001 | unpublished | Bt A13 | |
| Vip3Aa10 | Vip3V | AAN60738 | Doss et al | 2002 | Protein Expr. Purif. 26, 82-88 | Bt | |
| Vip3Aa11 | Vip3A | AAR36859 | Liu et al | 2003 | unpublished | Bt C9 | |
| Vip3Aa12 | Vip3A-WB5 | AAM22456 | Wu and Guan | 2003 | unpublished | Bt | |
| Vip3Aa13 | Vip3A | AAL69542 | Chen et al | 2002 | Sheng Wu Gong Cheng Xue Bao 18, 687-692 | Bt S184 | |
| Vip3Aa14 | Vip | AAQ12340 | Polumetla et al | 2003 | unpublished | Bt tolworthi | |
| Vip3Aa15 | Vip3A | AAP51131 | Wu et al | 2004 | unpublished | Bt WB50 | |
| Vip3Aa16 | Vip3LB | AAW65132 | Mesrati et al | 2005 | FEMS Micro Lett 244, 353-358 | Bt | |
| Vip3Aa17 | Jav90 | | Feitelson et al | 1999 | U.S. Pat. No. 6,603,063 August 2003 | Javelin 1990 | WO9957282(A2, A3) 11 Nov 1999 |
| Vip3Aa18 | | AAX49395 | Cai and Xiao | 2005 | unpublished | Bt 9816C | |
| Vip3Aa19 | Vip3ALD | DQ241674 | Liu et al | 2006 | unpublished | Bt AL | |
| Vip3Aa19 | Vip3A-1 | DQ539887 | Hart et al | 2006 | unpublished | | |
| Vip3Aa20 | Vip3A-2 | DQ539888 | Hart et al | 2006 | unpublished | | |
| Vip3Aa21 | Vip | ABD84410 | Panbangred | 2006 | unpublished | Bt aizawai | |
| Vip3Aa22 | Vip3A-LS1 | AAY41427 | Lu et al | 2005 | unpublished | Bt LS1 | |
| Vip3Aa23 | Vip3A-LS8 | AAY41428 | Lu et al | 2005 | unpublished | Bt LS8 | |
| Vip3Aa24 | | BI 880913 | Song et al | 2007 | unpublished | Bt WZ-7 | |
| Vip3Aa25 | | EF608501 | Hsieh et al | 2007 | unpublished | | |
| Vip3Aa26 | | EU294496 | Shen and Guo | 2007 | unpublished | Bt TF9 | |

APPENDIX A-continued

List of delta-endotoxins - from Crickmore et al. website (cited in application)
Accession Number is to NCBI entry

| | | | | | | | |
|---|---|---|---|---|---|---|---|
| Vip3Aa27 | | EU332167 | Shen and Guo | 2007 | unpublished | Bt 16 | |
| Vip3Aa28 | | FJ494817 | Xiumei Yu | 2008 | unpublished | Bt JF23-8 | |
| Vip3Aa29 | | FJ626674 | Xieumei et al | 2009 | unpublished | Bt JF21-1 | |
| Vip3Aa30 | | FJ626675 | Xieumei et al | 2009 | unpublished | MD2-1 | |
| Vip3Aa31 | | FJ626676 | Xieumei et al | 2009 | unpublished | JF21-1 | |
| Vip3Aa32 | | FJ626677 | Xieumei et al | 2009 | unpublished | MD2-1 | |
| Vip3Ab1 | Vip3B | AAR40284 | Feitelson et al | 1999 | U.S. Pat. No. 6,603,063 August 2003 | Bt KB59A4-6 | WO9957282(A2, A3) 11 Nov 1999 |
| Vip3Ab2 | Vip3D | AAY88247 | Feng and Shen | 2006 | unpublished | Bt | |
| Vip3Ac1 | PS49C | | Narva et al | — | US application 20040128716 | | |
| Vip3Ad1 | PS158C2 | | Narva et al | — | US application 20040128716 | | |
| Vip3Ad2 | ISP3B | CAI43276 | Van Rie et al | 2005 | unpublished | Bt | |
| Vip3Ae1 | ISP3C | CAI43277 | Van Rie et al | 2005 | unpublished | Bt | |
| Vip3Af1 | ISP3A | CAI43275 | Van Rie et al | 2005 | unpublished | Bt | |
| Vip3Af2 | Vip3C | ADN08753 | Syngenta | — | WO 03/075655 | | |
| Vip3Ag1 | Vip3B | ADN08758 | Syngenta | — | WO 02/078437 | | |
| Vip3Ag2 | | FJ556803 | Audtho et al | 2008 | | Bt | |
| Vip3Ah1 | Vip3S | DQ832323 | Li and Shen | 2006 | unpublished | Bt | |
| Vip3Ba1 | | AAV70653 | Rang et al | 2004 | unpublished | | |
| Vip3Bb1 | Vip3Z | ADN08760 | Syngenta | — | WO 03/075655 | | |
| Vip3Bb2 | | EF439819 | Akhurst et al | 2007 | | | |

We claim:

1. A transgenic plant comprising DNA encoding a Cry1Ab insecticidal protein, DNA encoding a Cry1Be insecticidal protein, and DNA encoding a Cry1Fa insecticidal protein, wherein said Cry1Be insecticidal protein comprises SEQ ID NO:1 and said Cry1Ab insecticidal protein comprises SEQ ID NO:2, and wherein said Cry1Ab and said Cry1Be insecticidal proteins have different receptor binding sites in fall armyworm gut.

2. The transgenic plant of claim 1, said plant further comprising DNA encoding a fourth insecticidal protein selected from the group consisting of Cry2A, Cry1I, DIG-3, Vip3Ab, Cry1Ca and Cry1E.

3. A seed of the plant of claim 1.

4. A plurality of plants comprising non-Bt refuge plants and plants of claim 1, wherein said refuge plants comprise less than 40% of said plurality of plants.

5. The plurality of plants of claim 4, wherein said refuge plants comprise less than 30% of said plurality of plants.

6. The plurality of plants of claim 4, wherein said refuge plants comprise less than 20% of said plurality of plants.

7. The plurality of plants of claim 4, wherein said refuge plants comprise less than 10% of said plurality of plants.

8. The plurality of plants of claim 4, wherein said refuge plants comprise less than 5% of said plurality of plants.

9. A mixture of seeds comprising refuge seeds from non-Bt refuge plants, and a plurality of the seeds of claim 3, wherein said refuge seeds comprise less than 40% of all the seeds in the mixture.

10. The mixture of seeds of claim 9, wherein said refuge seeds comprise less than 30% of all the seeds in the mixture.

11. The mixture of seeds of claim 9, wherein said refuge seeds comprise less than 20% of all the seeds in the mixture.

12. The mixture of seeds of claim 9, wherein said refuge seeds comprise less than 10% of all the seeds in the mixture.

13. The mixture of seeds of claim 9, wherein said refuge seeds comprise less than 5% of all the seeds in the mixture.

14. A method of managing development of resistance to a Cry protein by a fall armyworm, said method comprising planting seeds to produce the plurality of plants of claim 4.

15. The method of claim 14, wherein said seeds are planted so that the resulting plants occupy more than 10 acres.

16. The plant of claim 1, wherein said plant is selected from the group consisting of corn, soybeans, and cotton.

17. The plant of claim 16, wherein said plant is a corn plant.

18. A plant cell of the plant of claim 1, wherein said plant cell comprises said DNA encoding said Cry1Be insecticidal protein, said DNA encoding said Cry1Ab insecticidal protein, and said DNA encoding a Cry1Fa insecticidal protein.

19. A method of controlling a fall armyworm insect, said method comprising plating a seed comprising DNA encoding a Cry1Be insecticidal protein, a Cry1Ab insecticidal protein and a Cry1Fa insecticidal protein, wherein said Cry1Ab and said Cry1Be insecticidal proteins have different receptor binding sites in fall armyworm gut.

\* \* \* \* \*